(12) United States Patent
Li et al.

(10) Patent No.: US 9,469,625 B2
(45) Date of Patent: Oct. 18, 2016

(54) ORGANIC COMPOUNDS

(75) Inventors: Peng Li, New York, NY (US); Youyi Peng, New York, NY (US); John Tomesch, New York, NY (US); Lawrence P. Wennogle, New York, NY (US); Qiang Zhang, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 14/128,378

(22) PCT Filed: Jun. 22, 2012

(86) PCT No.: PCT/US2012/043880
§ 371 (c)(1),
(2), (4) Date: Mar. 24, 2014

(87) PCT Pub. No.: WO2012/178112
PCT Pub. Date: Dec. 27, 2012

(65) Prior Publication Data
US 2014/0205596 A1     Jul. 24, 2014

Related U.S. Application Data

(60) Provisional application No. 61/501,207, filed on Jun. 25, 2011.

(51) Int. Cl.
| | | |
|---|---|---|
| *A61K 31/445* | (2006.01) | |
| *C07D 401/12* | (2006.01) | |
| *A61K 31/454* | (2006.01) | |
| *A61K 31/4745* | (2006.01) | |
| *A61K 31/506* | (2006.01) | |
| *A61K 33/24* | (2006.01) | |
| *A61K 45/06* | (2006.01) | |

(52) U.S. Cl.
CPC ........... *C07D 401/12* (2013.01); *A61K 31/454* (2013.01); *A61K 31/4745* (2013.01); *A61K 31/506* (2013.01); *A61K 33/24* (2013.01); *A61K 45/06* (2013.01)

(58) Field of Classification Search
USPC ................... 514/326, 283, 49; 546/210, 211
See application file for complete search history.

(56) References Cited

U.S. PATENT DOCUMENTS

| | | | | |
|---|---|---|---|---|
| 7,799,782 | B2 * | 9/2010 | Munson et al. | ........... 514/234.5 |
| 9,108,949 | B2 | 8/2015 | Peng et al. | |
| 2004/0147522 | A1 | 7/2004 | Wong et al. | |
| 2004/0220170 | A1* | 11/2004 | Atkinson et al. | .......... 514/210.2 |
| 2006/0019984 | A1 | 1/2006 | Groppi et al. | |
| 2010/0152232 | A1 | 6/2010 | Mazurov et al. | |
| 2010/0179186 | A1 | 7/2010 | Papke et al. | |
| 2014/0205596 | A1 | 7/2014 | Li et al. | |

FOREIGN PATENT DOCUMENTS

| | | |
|---|---|---|
| WO | WO 03/037274 | 5/2003 |
| WO | WO 2004/099154 | 11/2004 |
| WO | WO 2005/000821 | 1/2005 |
| WO | WO 2009/112459 A1 | 7/2010 |
| WO | WO 2012/178112 | 12/2012 |

OTHER PUBLICATIONS

Peng et al., Bioorganic & Medicinal Chemistry Letters, 2010, 20:4825-4830.*
Atkinson et al. CAS: 141:395577, 2004.*
Lukas, R. J. et al, *Pharmacol. Rev.*, 51, 397-401 (1999).
Flores, C. et al., *Mol. Pharmacol.*, 41, 31-37 (1992).
Lindstrom J. et al, *Prog. Brain Res.*, 109, 125-137 (1996).
Arneric, S.P. et al, *Biochem. Pharmacol.*, 74, 1092-1101 (2007).
Mazurov A. et al, *Curr. Med. Chem.*, 13, 1567-1584 (2006).
Olincy A., *Arch. Gen. Psychiatry*, 63, 630-638 (2006).
Chang, C. C, et al. *J. Biomed. Sci.*, 6, 368-375 (1999).
Davies, A. R., et al., *Neuropharmacology*, 38, 679-690 (1999).
Jensen, A. A., et. al. *J. Med. Chem.*, 48, 4705-4745 (2005).
Sciamanna, J. *Neurochem.* 69, 2302-2311 (1997).
Paleari, et al. *Int. J. Cancer.* 125, 199-211 (2009).
Buckingham et al, *Pharmacological Reviews*, vol. 61 No. 1, 39-61 (2009).
Jones, et al, *J Mol Neurosci.*, 30 (1-2):83-84 (2006).
Roncarati, *J Pharmacol Exp Ther.*, 329(2):459-468. (May 2009, Epub Feb. 17, 2009).
Papke, et al., Journal of Pharmacology and Experimental Therapeutics, vol. 329 No. 2 791-807 (2009).
Peng, et al., "Discovery of Novel alpha7 Nicotinic Receptor Antagonists", *Bioorganic & Medicinal Chemistry Letters* 20, pp. 4825-4830 (2010).
Henchman, et al., "Ligand-Induced Conformational Change in the alpha7 Nicotinic Receptor Ligand Binding Domain", *Biophysical Journal*, vol. 88(4), pp. 2564-2576 (2005).
Rodriguez, et al., "Click Chemistry on Solid Phase: Parallel Synthesis of N-Benzyltriazole Carbxamides as Super-Potent G-Protein Coupled Receptor Ligands," *Journal of Combinatorial Chemistry*, 8(2), 252-261 (2006).
Registry [STN online], entered May 29, 2011, RN:1302490-94-3.
Registry [STN online], entered May 24, 2011, RN:1299716-67-8.
Registry [STN online], entered May 18, 2011, RN:1296508-55-8.
Registry [STN online], entered May 5, 2011, RN:1290550-37-6.
Registry [STN online], entered May 5, 2011, RN:1290321-74-2.
Registry [STN online], entered May 5, 2011, RN:1290321-69-5.
Registry [STN online], entered May 3, 2011, RN:1289322-69-5.
Registry [STN online], entered May 2, 2011, RN:1288944-52-4.
Registry [STN online], entered Apr. 29, 2011, RN:1287554-44-2.
Registry [STN online], entered Apr. 13, 2011, RN:1279270-42-6.
Registry [STN online], entered Apr. 12, 2011, RN:1279078-00-0.
Registry [STN online], entered Apr. 10, 2011, RN:1277798-76-1.
Registry [STN online], entered Apr. 10, 2011, RN:1277737-34-4.
Registry [STN online], entered Apr. 10, 2011, RN:1277736-60-3.
Registry [STN online], entered Apr. 10, 2011, RN:1277529-93-7.

(Continued)

*Primary Examiner* — Rei-Tsang Shiao
(74) *Attorney, Agent, or Firm* — Hoxie & Associates LLC

(57) ABSTRACT

The invention relates to compounds and methods of treatment relating to nicotinic receptor antagonists. For example, the compounds and methods of treatment function block the activity of certain acetylcholine receptors and subtypes therein, and are useful treating diseases and conditions mediated by nicotinic receptor stimulation, e.g., small cell lung cancer.

34 Claims, No Drawings

(56) References Cited

OTHER PUBLICATIONS

Registry [STN online], entered Jan. 28, 2011, RN:1260998-72-8.
Registry [STN online], entered Sep. 17, 2010, RN:1241973-12-5.
Registry [STN online], entered Mar. 25, 2010, RN:1214456-33-3.
Registry [STN online], entered Feb. 22, 2010, RN:1207057-14-4.
Registry [STN online], entered Feb. 22, 2010, RN:1207020-03-8.
Registry [STN online], entered Jul. 30, 2009, RN:1170376-73-4.
Registry [STN online], entered Apr. 15, 2009, RN:1135071-68-9.
Registry [STN online], entered Nov. 2, 2008, RN:1069822-46-3.
Registry [STN online], entered Sep. 26, 2008, RN:1053148-42-7.
Registry [STN online], entered Jun. 1, 2008, RN:1024146-34-6.
Registry [STN online], entered Mar. 13, 2008, RN:1007754-83-7.
Registry [STN online], entered Oct. 26, 2007, RN:951602-39-4.
Nishioka, et al., "Sensitization of Epithelial Growth Factor Receptors by Nicotine Exposure to Promote Breast Cancer Cell Growth," *Breast Cancer Research*, vol. 13(6), R113, pp. 1-11 (2011).
Sacco, et al., "Nicotinic Receptor Mechanisms and Cognition in Normal States and Neuropsychiatric Disorders," *Journal of Psychopharmacology*, vol. 18(4), pp. 457-474 (2004).
Singh, et al., "Nicotinic Acetylcholine Receptor Signaling in Tumor Growth and Metastasis," *Journal of Oncology*, vol. 2011 (2011).
Spindel, et al., "Is Nicotine the Estrogen of Lung Cancer?" *American Journal of Respiratory and Critical Care Medicine*, vol. 179, p. 1081 (2009).

\* cited by examiner

ORGANIC COMPOUNDS

CROSS REFERENCE TO RELATED APPLICATIONS

This application is a national stage application under 35 U.S.C. §371 of PCT/US2012/043880, filed on Jun. 22, 2012, which claims the benefit of PCT/US2011/041866 filed Jun. 24, 2011 and U.S. Provisional Application No. 61/501,207 filed, Jun. 25, 2011, the contents of each of which are incorporated herein by reference in their entireties.

STATEMENT REGARDING GOVERNMENT FUNDING

This invention was made, in part, with government support under Grants No. R43 MH067488-01 and R01 GM57484 awarded by the National Institutes of Health, and Grants No. DAMD 17-03-2-0019 and W81XWH-06-C-0013 awarded by the United States Army Medical Research and Material Command NETRP. The government has certain rights in the invention.

TECHNICAL FIELD

The field generally relates to organic compounds that act as nicotinic receptor antagonists. The field further relates to the use of nicotinic receptor antagonists for use as a prophylaxis and/or treatment for both small and non-small cell lung cancer, HIV, cognitive disorders, Alzheimer's disease, smoking cessation, Schizophrenia, and mammalian exposure to various neurological toxins.

BACKGROUND OF THE INVENTION

Nicotinic acetylcholine receptors (nAChRs) belong to the Cys-loop subfamily of pentameric ligand-gated ion channels and can be classified into muscle-type and neuronal subtypes. The neuronal nAChRs comprise twelve subunits ($\alpha 2$-$\alpha 10$ and $\beta 2$-$\beta 4$) with different arrangements, while the muscle-type is consisted of four subunits in a single arrangement of $\alpha 1 \gamma \alpha 1 \beta 1 \delta$ (c is replaced by e in the adult). (Lukas, R. J. et al., *Pharmacol. Rev.* 1999, 51, 397) Two major neuronal receptors a4b2 and $\alpha 7$ have been identified in the central nervous system. (Flores, C. et al., *Mol. Pharmacol.* 1992, 41, 31; Lindstrom J. et al., *Prog. Brain Res.* 1996, 109, 125) The neuronal $\alpha 7$ nAChR has been proposed as a potential therapeutic target for a broad range of neurodegenerative and psychiatric diseases, including Alzheimer's disease, schizophrenia, anxiety, and epilepsy. A variety of selective partial and full agonists have been developed for the $\alpha 7$ nAChR as potential therapeutics. (Jensen A. et al., *Prog., Brain Res.* 1996) Several $\alpha 7$ nAChR selective agonists (e.g., TC-5619 and MEM-3454) have advanced to clinical trials for Alzheimer's disease and schizophrenia. (Arneric, S. P. et al., *Biochem. Pharmacol.* 2007, 74, 1092; Mazurov A. et al., *Curr. Med. Chem.* 2006, 13, 1567; Olincy A., *Arch. Gen. Psychiatry* 2006, 63, 630) Although extensive efforts have been taken to identify selective $\alpha 7$ nAChR agonists, the development of $\alpha 7$ selective antagonists is relatively limited. Some studies have reported that certain naturally derived compounds may be incorporated as $\alpha 7$ selective antagonists. For example, the krait *Bungarus multicinctus* derived peptide toxin a-bungarotoxin ($\alpha$-BTX) and the seeds of Delphinum isolated nonpetide toxin methyllycaconitine (MLA) are two frequently used $\alpha 7$ selective antagonists. (Chang, C. C., et al. *J. Biomed. Sci.* 1999, 6, 368; Davies, A. R., et al. *Neuropharmacology* 1999, 38, 679)

Unfortunately, $\alpha$-BTX is a potent antagonist for muscle-type nAChRs as well, and both compounds also inhibit nAChR subtypes $\alpha 9$ and $\alpha 9 \alpha 10$. (Jensen, A. A., et. al. *J. Med. Chem.* 2005, 48, 4705) Nevertheless, subtype-selective antagonists may possess intrinsic value as tools to define the roles played by $\alpha 7$ nAChRs in the physiological and pathophysiological processes.

Indeed, and along these same lines, nicotinic acetylcholine receptors have been implicated as possible drug targets in a myriad of various disease states and for use as a possible measure for counter-terrorism purposes.

For example, with regards to various disease states, nAChRs have for some time now been studied in an attempt to find a possible nexus between targeting of the receptor and treatment of small cell lung carcinoma (SCLC). (Sciamanna, *J. Neurochem.* 69, 2302-2311 1997). While SCLC is a neuroendocrine neoplasm that accounts for a minority of newly diagnosed lung cancers, roughly a quarter, it is quite deadly and patients generally die within a mere year of being diagnosed. Thus, there is a pertinent need for the development of treatments, or means of prophylaxis, that can be administered to a patient in order to mitigate, or achieve complete ablation of, the SCLC disease state.

Despite the attendant need, few, if any, specific treatments are available for SCLC. However, the most current data available in the field indicates that two types of nAChRs can regulate NA and CA influx. Such regulation of calcium and sodium influx has biological and therapeutic ramifications in the treatment of neuroendocrine neoplasms. Thus, in light of the paucity of compounds available that can effectively and specifically target such channels, there still remains a glaring need for rationally based compounds that have the ability to target such receptors.

In addition to developing a more efficacious means for treating SCLC, there is also an attendant need for compounds that may be used to treat the more widespread dilemma of non-small cell lung cancer (NSCLC). In this regard it has been observed that mesothelioma and non-small cell lung cancer express functional nAChR. (Paleari, et al. *Int. J. Cancer*: 125, 199-211 2009) Thus, there has been speculation that nicotine may play some heretofore-unknown role in contributing to lung cancer pathogenesis via activation of such cellular proliferation pathways as Akt signaling or by inhibiting other natural cellular apoptotic machinery. (Id) However, some studies have indicated that nicotine acts on nAChRs, expressed in NSCLC tumor cells, by activating a proliferative response in such cells. (Id)

Next, despite their distinct disease pathology, it has been discovered that disease states such as cancer and AIDS have a common link via nAChRs. In addition to the need to develop treatments for both small and non-small cell lung cancer, however, there is also a need for compounds or treatment mechanisms that have the ability to effectively combat HIV and AIDS, disease states that also pose a very serious threat to public health worldwide. In fact more than 40 million people are infected worldwide with HIV-1 and an estimated 14,000 new infections occur every day. Since the first cases of AIDS were identified in 1981 the deaths of over 25 million people have been attributed to HIV/AIDS.

As mentioned, alpha-7 nAChRs has been found in lung cancer cells where activation by either natural molecules or compounds in tobacco smoke are shown to promote cancer growth. It has been found that those same alpha-7 nAChRs are upregulated in immune cells in AIDS. This suggests that over activation of alpha-7 receptors in macrophages by the AIDS virus protein, may cause premature cell death. Thus, and at the very least, antagonists to nAChRs are needed to continue to exploit the relationship between cancer, AIDS and nAChR activity, and thus provide treatments for these disease states.

Additionally, nicotinic acetylcholine receptors have been also been implicated to play a role in neurodegenerative diseases and cognitive disease or disorders. For example, nicotinic acetylcholine receptors have been implicated in disease such as Alzheimer's disease. Buckingham et al, Pharmacological Reviews March 2009 vol. 61 no, 1 39-61. Moreover, a7 nAChR have specifically been identified as playing flail some type of role in the etiology and/or pathology of Alzheimer's disease. Jones I W, et al, J Mol Neurosci. 2006; 30 (1-2):83-4.

Nicotinic acetylcholine receptors have been also been suggested to play a role in certain neurodegenerative and cognitive disorders. The alpha7 nicotinic acetylcholine receptor (nAChR) has been thought of as a target for treatment of cognitive dysfunction associated with Alzheimer's disease and schizophrenia. *J Pharmacol Exp Ther.* 2009 May; 329(2):459-68. Epub 2009 Feb. 17.

However, despite these suggested links to a number of disparate diseases and disorders, there are attendant issues with nicotinic acetylcholine receptors. For example nicotinic acetylcholine receptors represent a complex and diverse set of receptor subtypes. Additionally, prolonged use may lead to desensitization of the receptor. Papke, et al., *Journal of Pharmacology and Experimental Therapeutics*, May 2009 vol. 329 no. 2 791-807.

These latter factors have made it difficult to work with nicotinic acetylcholine receptors and to develop compounds that are efficacious both in the short and long term.

SUMMARY OF THE INVENTION

It is an aspect of the present invention that the novel nicotinic acetylcholine receptor antagonists disclosed herein may be used in a broad array of clinical, medicinal, or pharmaceutical facets.

It is contemplated by the present invention that the compounds and formulas disclosed herein could act as novel Alpha 7 (α7) nicotinic acetylcholine receptor antagonists.

It is an object of the present invention that the nicotinic receptor antagonists disclosed herein are believed to possess reversible binding properties. Moreover, the compounds of the present invention are selective for α7 nAChR. For example, the compounds of the present invention are not believed to bind to α4β2 nAChR neuromuscular receptors.

In one aspect of the present invention, the novel nicotinic receptors disclosed herein are less lipophilic and more polar than nicotinic acetylcholine receptor antagonists that have previously been disclosed or known in the prior art. Compared to other nicotinic acetylcholine receptor antagonists known in the art, and without being bound to any theory, the polar substitutions of the nicotinic acetylcholine receptor antagonists disclosed herein render these compounds less likely to cross the Blood Brain Barrier and, thus, less likely to have adverse central nervous system side effects.

It is further contemplated that the novel nicotinic receptor antagonists of the present invention will be active in the peripheral nervous system as potent nicotinic receptor antagonists. One benefit, of many, of the novel nicotinic receptor antagonists disclosed herein, is that said antagonists retain their potent activity in the peripheral nervous system while simultaneously lacking central nervous system toxicity.

For example, it is contemplated that the nicotinic receptor antagonists of the present invention may be used to inhibit the growth cycle of non-small cell lung cancer cells.

It is also contemplated that the nicotinic receptor antagonists of the present invention will be used as a counter measure to treat exposure, or potential exposure, to a wide array of potential neurotoxins. The AChRs are activated by acetylcholine (ACh), which is hydrolyzed to choline by acetylcholineesterase (AChE). When AChE is irreversibly inhibited by organophosphorus nerve agents like DFP and sarin, the uncontrolled accumulation of ACh at peripheral and central muscarinic AChRs (mAChRs) and nAChRs causes the cholinergic syndrome. This syndrome is characterized by sweating, pupillary constriction, convulsions, tachycardia, and eventually death.

The currently acknowledged treatment for nerve agent intoxication is the mAChR antagonist atropine used in concert with an oxime reactivator of AChE (e.g., pralidoxime). However, while this treatment regimen does not directly target nicotinic receptors both mAChRs and nAChRs are involved in nerve agent toxicity.

It is contemplated that the novel nicotinic receptor antagonists of the present invention could provide neuroprotection against seizure-like behaviors induced by DFP and, therefore, may be useful for treatment of organophosphus nerve agent intoxication. Moreover, it is also contemplated that the novel nicotinic receptor antagonists disclosed herein provide a means of discerning between the physiological roles of neuronal α7 nAChR under normal and diseased states, and may be used as diagnostic tools used for discovering potential therapies for organophosphorus nerve agent intoxication.

However, without being bound by any theory, it is also believed that while the compounds of the present invention are selective α7 nAChR antagonists, that this does not also mean that the compounds activity is overall anticholinergic. Indeed, and again without being bound by any theory, it is theorized that these selective antagonists possibly enhance cognition, particularly at lower doses. Without being bound by theory, it is hypothesized that at lower doses or over extended periods, that the compounds disclosed herein may reduce desensitization in response to acetylcholine, which thereby possibly enhances the effects of endogenous acetylcholine.

In still another aspect of the present invention the novel nicotinic receptor antagonists disclosed herein could be used, either alone or combination with another pharmaceutical, to treat Alzheimer's disease. It is contemplated that the present invention may also treat the symptoms of Alzheimer's disease. In one aspect it is contemplated the present invention may be used to treat at least one symptom of Alzheimer's disease.

It is contemplated by the present invention the compounds disclosed herein may be used treat Parkinson's disease and/or the symptoms of Parkinson's disease. It is contemplated that diminished or reduced cognition may be a symptom of Parkinson's disease, or may be a symptom of a medication taken to alleviate the symptoms or treat Parkinson's disease.

It is contemplated by the present invention that the nicotinic receptor antagonists disclosed herein may also treat at least one symptom of Alzheimer's disease wherein that symptom of Alzheimer's disease relates to cognitive impairment.

In another aspect of the present invention it is contemplated that the novel nicotinic receptor antagonists disclosed herein could be used to treat or prevent relapse of opioid, cocaine, nicotine, and methamphetamine use. For example, it is contemplated that the novel nicotinic receptor antagonists disclosed herein could be used to in treatments directed toward smoking cessation.

In yet another aspect, it is contemplated that the novel nicotinic receptor antagonists disclosed herein could be used to treat and/or improve cognition and/or cognition related diseases or disorders.

It is further contemplated that the compounds of the present invention may be used to treat dementia. In one embodiment the compounds of the present invention may be used to treat psychosis, e.g., in schizophrenia, schizoaffective disorder, schizophreniform disorder, psychotic disorder, delusional disorder, mania or bipolar disorder.

It is also contemplated that the compounds of the present invention may be used to treat cognitive impairment wherein cognitive impairment is a result and/or symptom of psychosis, e.g., in schizophrenia, schizoaffective disorder, schizophreniform disorder, psychotic disorder, delusional disorder, mania or bipolar disorder.

In yet another aspect of the present invention the novel nicotinic receptor antagonists disclosed herein could be used to have a protective effect on patients in order to prevent sepsis.

As well, it also contemplated that the nicotinic receptor antagonists of the present invention could be used as means for prophylaxis or treatment of HIV and/or AIDS. In a preferred aspect, novel α7 nAChR selective antagonists are administered in an effective therapeutic dose causing some measure of reduced symptomology or total ablation of the disease state.

In another aspect of the present invention, it is further contemplated that novel α7 nAChR selective antagonists may be used as research or diagnostic tools. It is further contemplated that novel α7 nAChR selective antagonists could be used as a research tool in elucidating signal transduction in neuronal tissue. It is also contemplated that novel alpha7 nAChR selective antagonists could be used as a research tool in elucidating signal transduction pathway in non-neuronal tissue as well.

In another aspect of the present invention it is contemplated that the novel nicotinic receptor antagonists disclosed herein could be used to improve wound healing in patients. In is contemplated by the present invention that the novel nicotinic receptor antagonists disclosed herein could be used to improve wound healing in diabetics.

In yet another aspect of the present invention the novel nicotinic receptor antagonists disclosed herein could be used to have a protective effect on patients in order to prevent sepsis.

In another aspect of the present invention it is contemplated that the novel nicotinic receptor antagonists disclosed herein could be used to treat or prevent relapse of opioid, cocaine, nicotine, and methamphetamine use. For example, it is contemplated that the novel nicotinic receptor antagonists disclosed herein could be used to in treatments directed toward smoking cessation.

Compounds of the invention may exist in free or salt form, e.g. as acid addition salts. In the specification unless otherwise indicated language such as compounds or formulas or compounds of the invention are to be understood as embracing the compounds in any form, for example free or acid addition salt form, or where the compounds contain acid substituents, in base addition salt form. Or where compounds contain basic substituents, in acid addition salt form. The compounds disclosed herein are intended for use as pharmaceuticals, therefore pharmaceutically acceptable salts are preferred. Salts which are unsuitable for pharmaceutical uses may be useful, for example, for the isolation or purification of free compounds, formulas, or compounds of the invention or their pharmaceutically acceptable salts, are therefore also included.

It is contemplated the compounds disclosed herein may be used to improve cognition in patients wherein the reduced or diminished cognition is the result or side effect of a medication used to treat the primary illness (i.e. medications used to treat schizophrenia).

DETAILED DESCRIPTION OF THE INVENTION

The examples provided in the detailed description are merely examples, which should not be used to limit the scope of the claims in any claim construction or interpretation.

The present invention contemplates nicotinic acetylcholine receptor antagonists of Formula I:

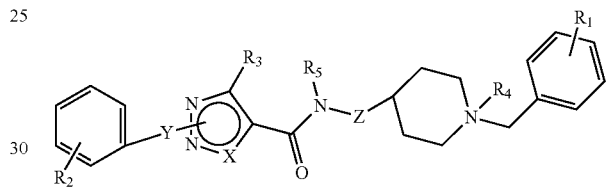

Formula I wherein $R_1$ and $R_2$ are independently halogen (e.g. Cl), —$SO_2NH_2$, or —COOH, e.g., in para- (4-) position, or H (i.e., phenyl is unsubstituted);

Y and Z are independently a bond or —$CH_2$—;

X is N or $CR_6$;

$R_3$, $R_5$ and $R_6$ are independently H, aryl, or lower (e.g. $C_{1-4}$) alkyl, e.g. methyl, ethyl or propyl;

$R_4$ is lower alkyl, e.g., methyl, or $R_4$ is not present;

in free or pharmaceutically acceptable salt form;

provided that when $R_4$ is lower alkyl, the compound forms a quaternary ammonium salt and there is an associated pharmaceutically acceptable anion present, e.g., halide, for example chloride, bromide or iodide.

For example, the invention provides compounds of Formula 1, as follows:

1.1. A compound of Formula I wherein $R_1$ is H.
1.2. A compound of Formula I wherein $R_1$ is —$SO_2NH_2$.
1.3. A compound of Formula I wherein $R_1$ is —COOH.
1.4. A compound of any of the preceding scopes wherein $R_2$ is —$SO_2NH_2$.
1.5. A compound of Formula I or 1.1, 1.2, or 1.3 wherein $R_2$ is H.
1.6. A compound of Formula I or 1.1, 1.2, or 1.3 wherein $R_2$ is —COOH.
1.7. A compound of any of the preceding scopes wherein X is N and Y is attached to the 2-nitrogen of the 1,2,3-triazole ring.
1.8. A compound of any of Formula I or 1.1-1.6 wherein X is N and Y is attached to the 1-nitrogen of the 1,2,3-triazole ring.
1.9. A compound of any of Formula I or 1.1-1.6 wherein X is C and Y is attached to the 2-nitrogen of the 1,2,3-triazole ring.

1.10. A compound of any of Formula I or 1.1-1.6 wherein X is C and Y is attached to the 1-nitrogen of the 1,2,3-triazole ring.
1.11. A compound of Formula I or any of the preceding scopes wherein $R_3$ is H.
1.12. A compound of Formula I or any of 1.1-1.10 wherein $R_3$ is aryl.
1.13. A compound of Formula I or any of 1.1-1.10, 1.12 wherein $R_3$ is phenyl or tolyl.
1.14. A compound of Formula I or any of 1.1-1.10, 1.12-1.13 wherein $R_3$ is phenyl.
1.15. A compound of Formula I or any of 1.1-1.10 or 1.12-1.13 wherein $R_3$ is tolyl.
1.16. A compound of Formula I or any of 1.1-1.1.10 wherein $R_3$ is lower (e.g. $C_{1-4}$) alkyl.
1.17. A compound of Formula I or any of 1.1-1.1.10, 1.16 wherein $R_3$ is methyl, ethyl, or propyl.
1.18. A compound of Formula I or any of the preceding scopes wherein $R_4$ is not present.
1.19. A compound of Formula I or any of 1.1-1.1.17 wherein $R_4$ is lower alkyl.
1.20. A compound of Formula I or any of 1.1-1.1.17 or 1.19 wherein $R_4$ is methyl.
1.21. A compound of Formula I or any of the preceding scopes wherein $R_5$ is H.
1.22. A compound of Formula I or any of 1.1-1.20 wherein $R_5$ is aryl.
1.23. A compound of Formula I or any of 1.1-1.20 or 1.22 wherein $R_5$ is phenyl or tolyl.
1.24. A compound of Formula I or 1.1-1.20 or 1.22-1.23 wherein $R_5$ is phenyl.
1.25. A compound of Formula I or any of 1.1-1.20 wherein $R_5$ is tolyl.
1.26. A compound of Formula I or any of 1.1-1.20 wherein $R_5$ is lower (e.g. $C_{1-4}$) alkyl
1.27. A compound of Formula I or any of 1.1-1.20 wherein $R_5$ is methyl, ethyl, or propyl.
1.28. A compound of Formula I or any of 1.1-20 or 1.27 wherein $R_5$ is methyl.
1.29. A compound of Formula I or any of 1.1-20 or 1.27 wherein $R_5$ is ethyl.
1.30. A compound of Formula I or any of 1.1-20 or 1.27 wherein $R_5$ is propyl.
1.31. A compound of Formula I or any of 1.1-1.30 wherein $R_6$ is H.
1.32. A compound of Formula I or any of 1.1-1.30 wherein $R_6$ is aryl.
1.33. A compound of Formula I or any of 1.1-1.30 or 1.32 wherein $R_6$ is phenyl or tolyl
1.34. A compound of Formula I or any of 1.1-1.30 or 1.32-1.33 wherein $R_6$ is phenyl
1.35. A compound of Formula I or any of 1.1-1.30 or 1.32-1.33 wherein $R_6$ is tolyl
1.36. A compound of Formula I or any of 1.1-1.35 wherein $R_6$ is lower (e.g. $C_{1-4}$) alkyl
1.37. A compound of Formula I or any of 1.1-1.36 wherein $R_6$ is methyl, ethyl, or propyl
1.38. A compound of Formula I or any of 1.1-1.37 wherein $R_6$ is methyl.
1.39. A compound of Formula I or any of 1.1-1.37 wherein $R_6$ is ethyl.
1.40. A compound of Formula I or any of 1.1-1.37 wherein $R_6$ is propyl.
1.41. Any of the preceding scopes wherein Y is methylene.
1.42. Any of the preceding scopes wherein Z is methylene.

For example, the invention provides compounds of Formula I or 1.1-1.42 wherein $R_1$ halogen.

For example, the invention provides compounds of Formula I or 1.1-1.42 wherein $R_1$ is chlorine.

For example, the invention provides compounds of Formula I or 1.1-1.42 wherein $R_1$ is flourine.

For example, the invention provides compounds of Formula I or 1.1-1.42 or any of [0030]-[0032] wherein $R_2$ halogen.

For example, the invention provides compounds of Formula I or 1.1-1.42 any of [0030]-[0032] wherein $R_2$ is chlorine.

For example, the invention provides compounds of Formula I or 1.1-1.42 any of [0030]-[0032] wherein $R_2$ is flourine.

For example, Compounds of Formula I include diazole compounds, e.g., compound 1-6:

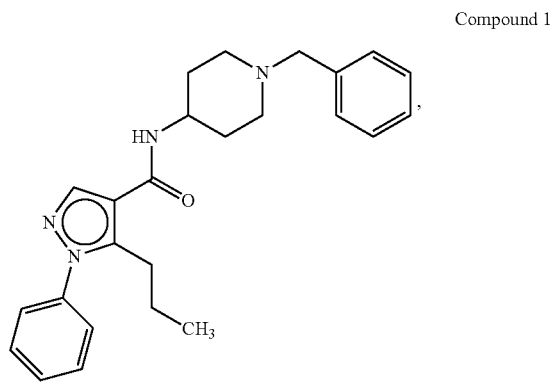

Compound 1

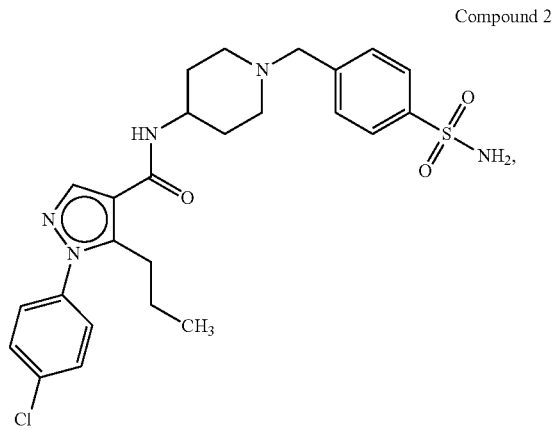

Compound 2

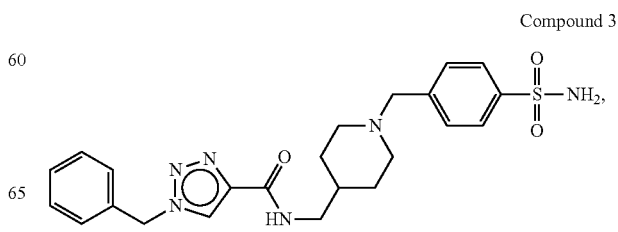

Compound 3

Compound 4
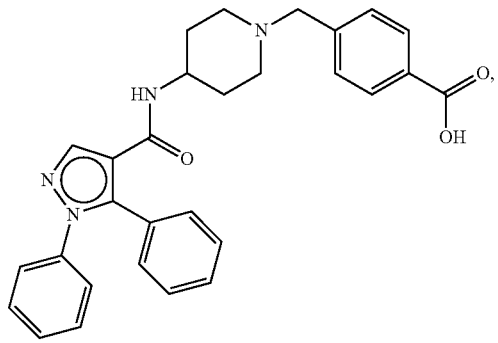
Compound 8
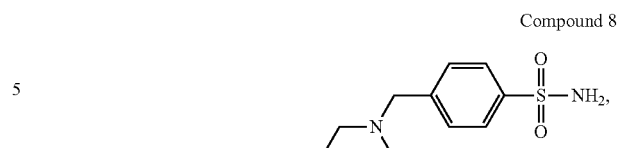
Compound 5
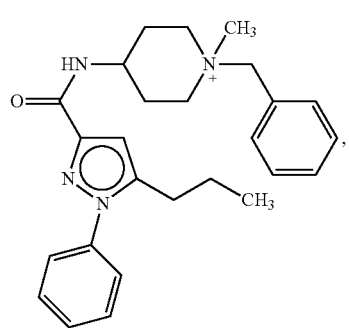
Compound 9
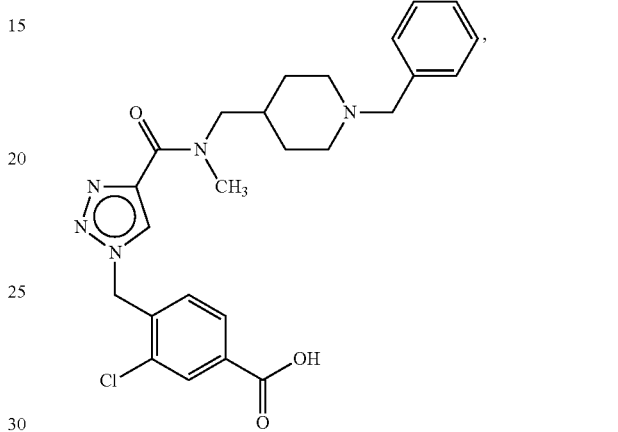
Compound 6
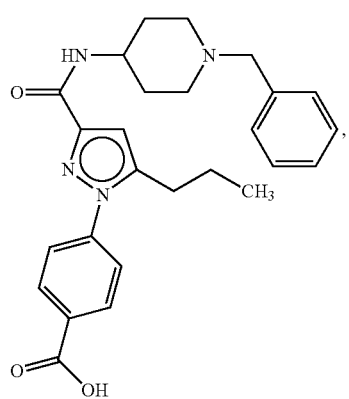
Compounds of Formula I also include triazole compounds, e.g., compounds 7-18:
Compound 10
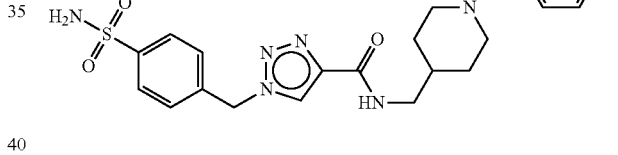
Compound 11
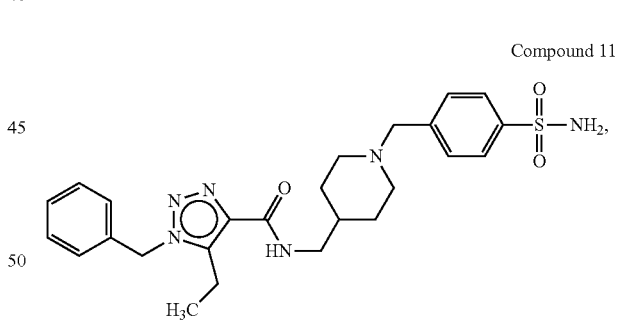
Compound 7
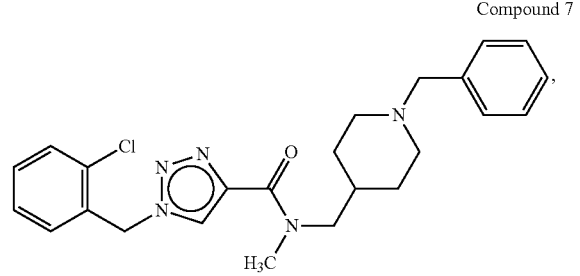
Compound 12
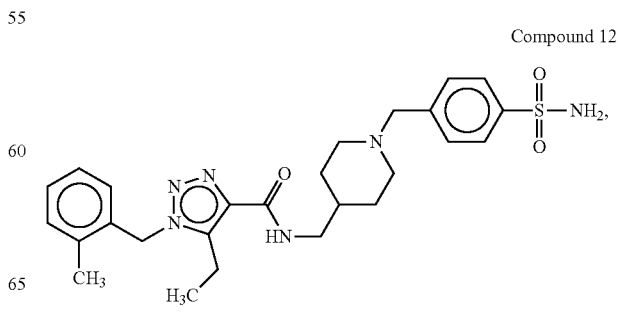

Compound 13

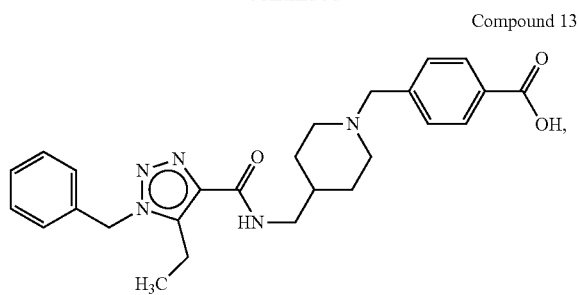

Compound 14

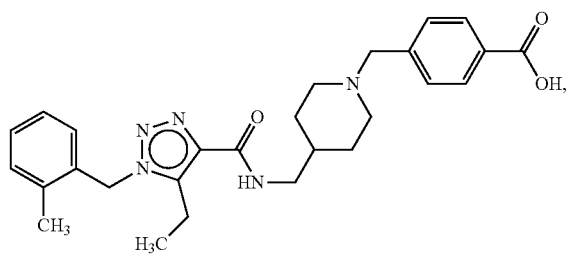

Compound 15

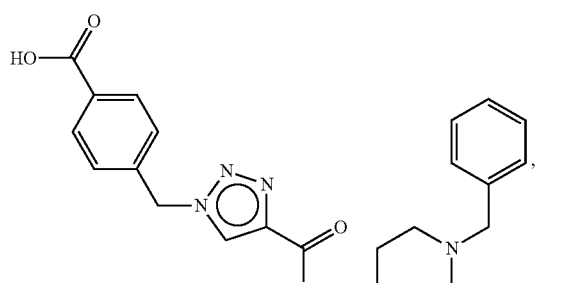

Compound 16

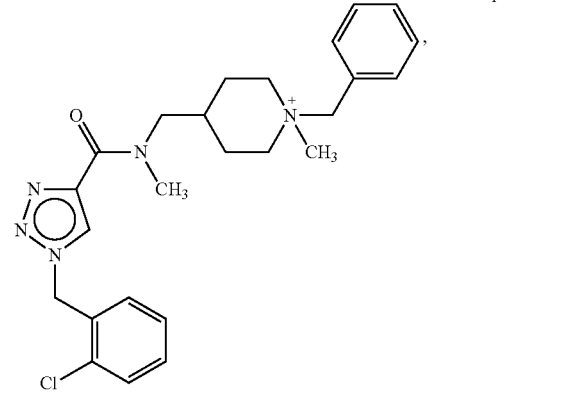

Compound 17

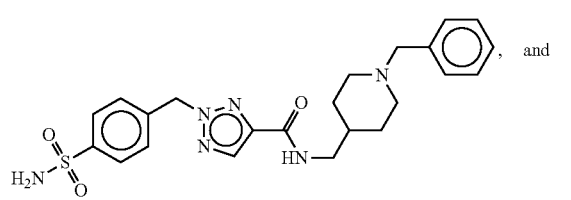

Compound 18

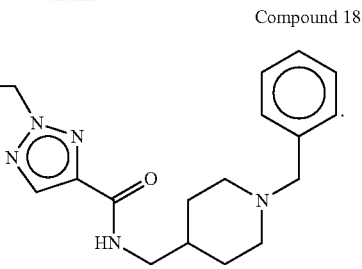

For example, Compounds of Formula I include compounds of Formula II:

Formula II

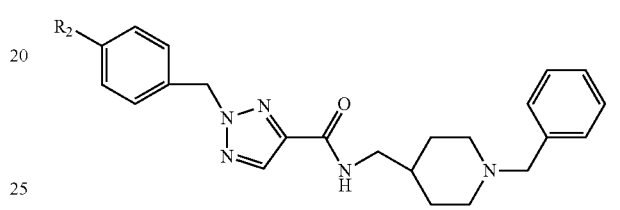

wherein $R_2$ is halogen (e.g. Cl or F), —SO$_2$NH$_2$, or —COOH, in free or pharmaceutically acceptable acid or base addition salt form, including quaternary ammonium salt form, e.g., methyl halide For example, the invention provides for compounds of Formula II as follows:

1.43 Formula II, wherein $R_2$ is halogen.
1.44 Formula II of 1.34, wherein $R_2$ is Cl.
1.45 Formula II or 1.34, wherein $R_2$ is Cl.
1.46 Formula II, wherein $R_2$ is —SO$_2$NH$_2$.
1.47 Formula II, wherein R2 is —COOH.

The present invention contemplates nicotinic acetylcholine receptor antagonists of Formula III:

Formula III

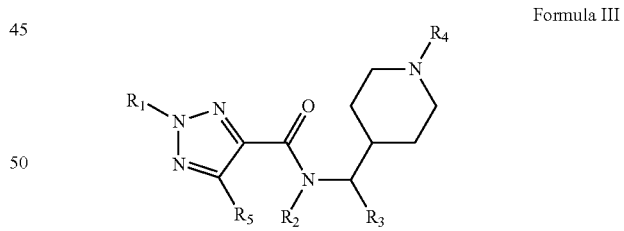

Wherein $R_1$ and $R_4$ are independently (e.g. $C_{1-4}$)alkyl, arylalkyl (e.g. benzyl), heteroalkyl, cycloalkyl, cycloalkylalky, or heteroaryl optionally substituted with halogen (e.g. Cl), —SO$_2$NH$_2$, or —COOH;

Wherein $R_2$, $R_3$, and $R_5$ are independently H, lower, (e.g. $C_{1-4}$) alkyl, or aryl (e.g. phenyl)

In free or salt form.

For example, the invention provides compounds of Formula III, as follows:

1.48. A compound of Formula III, wherein $R_1$ is arylalkyl.
1.49. A compound of Formula III, wherein $R_1$ is benzyl.
1.50. A compound of any of the preceding scopes wherein $R_4$ is arylalkyl.

1.51. A compound of any of the preceding scopes wherein $R_4$ is benzyl.
1.52. A compound of any of the preceding scopes wherein $R_2$ is H.
1.53. A compound of Formula III or any of 1.48-1.51 wherein $R_2$ is aryl.
1.54. A compound of Formula III or any of 1.48-1.51 or 1.53 wherein $R_2$ is phenyl or tolyl.
1.55. A compound of Formula III or any of 1.48-1.51 or 1.53 wherein $R_2$ is phenyl.
1.56. A compound of Formula III or any of 1.48-1.51 or 1.53 wherein $R_2$ is tolyl.
1.57. A compound of Formula III or any of 1.48-1.51 wherein $R_2$ is lower (e.g. $C_{1-4}$) alkyl.
1.58. A compound of Formula III or any of 1.57 wherein $R_2$ is methyl, ethyl, or propyl.
1.59. A compound of Formula III or any of 1.48-1.51 or 1.57 wherein $R_2$ is methyl.
1.60. A compound of Formula III or any of 1.48-1.51 or 1.57 wherein $R_2$ is ethyl.
1.61. A compound of Formula III or any of 1.48-1.51 or 1.57 wherein $R_2$ is propyl.
1.62. A compound of Formula III or any of the preceding scopes wherein $R_3$ is H.
1.63. A compound of Formula III or any of 1.48-1.61 wherein $R_3$ is aryl.
1.64. A compound of Formula III or 1.48-1.61 or 1.63 wherein $R_3$ is phenyl or tolyl.
1.65. A compound of Formula III or 1.48-1.61 or 1.63 wherein $R_3$ is phenyl.
1.66. A compound of Formula III or 1.48-1.61 or 1.63 wherein $R_3$ is tolyl.
1.67. A compound of Formula III or 1.48-1.61 wherein $R_3$ is lower (e.g. $C_{1-4}$) alkyl.
1.68. A compound of Formula III or 1.48-1.62 or 1.67 wherein $R_3$ is methyl, ethyl, or propyl.
1.69. A compound of Formula III or 1.48-1.62 or 1.68 wherein $R_2$ is methyl.
1.70. A compound of Formula III or 1.48-1.62 or 1.68 wherein $R_2$ is ethyl.
1.71. A compound of Formula III or 1.48-1.62 or 1.68 wherein $R_2$ is propyl.
1.72. A compound of Formula III or the preceding scopes wherein $R_5$ is H.
1.73. A compound of Formula III or 1.48-1.71 wherein $R_5$ is aryl.
1.74. A compound of Formula III or 1.48-1.71 or 1.73 wherein $R_5$ is phenyl or tolyl.
1.75. A compound of Formula III or 1.48-1.71 or 1.73 wherein $R_5$ is phenyl.
1.76. A compound of Formula III or 1.48-1.71 or 1.73 wherein $R_5$ is tolyl.
1.77. A compound of Formula III or 1.48-1.71 or 1.73 wherein $R_5$ is lower (e.g. $C_{1-4}$) alkyl
1.78. A compound of Formula III or 1.48-1.71 wherein $R_5$ is methyl, ethyl, or propyl.
1.79. A compound of Formula III or 1.48-1.71 or 1.78 wherein $R_5$ is methyl.
1.80. A compound of Formula III or 1.48-1.71 or 1.78 wherein $R_5$ is ethyl.
1.81. A compound of Formula III or 1.48-1.71 or 1.78 wherein $R_5$ is propyl.
1.82. A compound of Formula III or 1.48-1.81 wherein $R_1$ is arylalkyl optionally substituted with halogen.
1.83 A compound of Formula III or 1.48-1.82 wherein $R_1$ is arylalkyl optionally substituted with chlorine.
1.84 A compound of Formula III or any of 1.48-1.82, wherein $R_1$ is arylalkyl optionally substituted with fluorine.
1.85 A compound of Formula III or any of 1.48-1.84 wherein $R_1$ is benzyl optionally substituted with halogen.
1.86. A compound of Formula III or any of 1.48-1.84, wherein $R_1$ is benzyl optionally substituted with chlorine.
1.87. A compound of Formula III or any of 1.48-1.84, wherein $R_1$ wherein $R_1$ is benzyl optionally substituted with chlorine
1.88. A compound of Formula III or any of 1.48-1.81 wherein $R_1$ is arylalkyl optionally substituted with —$SO_2NH_2$.
1.89. A compound of Formula III or any of 1.48-1.81 or 1.88 wherein $R_1$ is benzyl optionally substituted with —$SO_2NH_2$.
1.90. A compound of Formula III or any of 1.48-1.81 wherein $R_1$ is arylalkyl optionally substituted with —COOH.
1.91. A compound of Formula III or any of 1.48-1.81 or 1.90 wherein $R_1$ is benzyl optionally substituted with —COOH.
1.92. A compound of Formula III or 1.48-1.81 wherein $R_4$ is arylalkyl optionally substituted with halogen.
1.93. A compound of Formula III or 1.48-1.82 wherein $R_4$ is arylalkyl optionally substituted with chlorine.
1.94. A compound of Formula III or any of 1.48-1.82, wherein $R_4$ wherein $R_1$ is arylalkyl optionally substituted with flourine.
1.95. A compound of Formula III or any of 1.48-1.84 wherein $R_4$ is benzyl optionally substituted with halogen.
1.96. A compound of Formula III or any of 1.48-1.84, wherein $R_4$ is benzyl optionally substituted with chlorine.
1.97. A compound of Formula III or any of 1.48-1.84, wherein $R_4$ wherein $R_1$ is benzyl optionally substituted with flourine.
1.98. A compound of Formula III or any of 1.48-1.81 wherein $R_4$ is arylalkyl optionally substituted with —$SO_2NH_2$.
1.99. A compound of Formula III or any of 1.48-1.81 or 1.88 wherein $R_4$ is benzyl optionally substituted with —$SO_2NH_2$.
1.100. A compound of Formula III or any of 1.48-1.81 wherein $R_4$ is arylalkyl optionally substituted with —COOH.
1.101. A compound of Formula III or any of 1.48-1.81 or 1.90 wherein $R_4$ is benzyl optionally substituted with —COOH.

For example, compounds of Formula III include compounds of Formula IV:

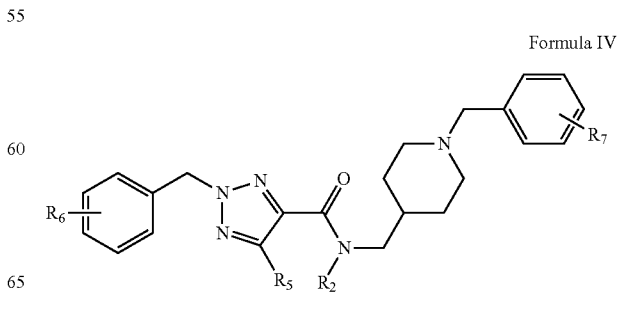

Formula IV

Wherein R₆ and R₇ are independently H (i.e. phenyl is unsubstituted), halogen (e.g. Cl), (e.g. $C_{1-4}$) alkyl, SO₂NH, COOR₈ (e.g. COOH), COR₈, CONRs, CONR₈R₉, SR₈, SOR₈, SO₂R₈;

Wherein R₈ and R₉ are independently H, (e.g. $C_{1-4}$) alkyl, cycloalkyl, aryl, or heteroaryl;

Wherein R₂, and R₅ are independently H, lower, (e.g. $C_{1-4}$) alkyl, or aryl (e.g. phenyl) in free or pharmaceutically acceptable acid or base addition salt form, including quaternary ammonium salt form, e.g., methyl halide For example, the invention provides compounds of Formula III, as follows:

1.102. A compound of Formula IV wherein R₆ is H.
1.103. A compound of Formula IV wherein R₆ is —SO₂NH₂.
1.104. A compound of Formula IV wherein R₆ is —COOH.
1.105. A compound of Formula IV wherein R₆ is Halogen.
1.106. A compound of Formula IV wherein R₆ is Cl.
1.107. A compound of Formula IV wherein R₆ is F.
1.108. A compound of Formula IV or 1.102-1.07 wherein R₇ is H.
1.109. A compound of Formula IV or 1.102-1.07 wherein R₇ is —SO₂NH₂.
1.110. A compound of Formula IV or 1.102-1.07 wherein R₇ is —COOH.
1.111. A compound of Formula IV or 1.102-1.07 wherein R₆ is Halogen.
1.112. A compound of Formula IV or 1.102-1.07 wherein R₆ is Cl.
1.113. A compound of Formula IV or 1.102-1.07 wherein R₆ is F.
1.114. A compound of Formula IV or any of any of the preceding scopes wherein R₆ is alkyl (e.g. $C_{1-4}$)
1.115. A compound of Formula IV or any of any of the preceding scopes wherein R₆ is methyl.
1.116. A compound of Formula IV or any of any of the preceding scopes wherein R₇ is alkyl (e.g. $C_{1-4}$)
1.117. A compound of Formula IV or any of any of the preceding scopes wherein R₇ is methyl.
1.118. A compound of Formula IV or 1.102-1.117 wherein R₂ is H.
1.119. A compound of Formula IV or 1.102-1.117 wherein R₂ is aryl.
1.120. A compound of Formula IV or 1.102-1.117 or 1.119 wherein R₂ is phenyl or tolyl.
1.121. A compound of Formula IV or 1.102-1.117, 1.119 or 1.120 wherein R₂ is phenyl.
1.122. A compound of Formula IV or 1.102-1.117, 1.119 or 1.120 wherein R₂ is tolyl.
1.123. A compound of Formula IV or 1.102-1.117 wherein R₂ is methyl, ethyl, or propyl.
1.124. A compound of Formula IV or any of 1.102-1.117 or 1.123 wherein R₂ is methyl.
1.125. A compound of Formula IV or any of 1.102-1.117 or 1.123 wherein R₂ is ethyl.
1.126. A compound of Formula IV or any of 1.102-1.117 or 1.123 wherein R₂ is propyl
1.127. A compound of Formula IV or 1.102-1.126 wherein R₅ is H.
1.128. A compound of Formula IV or 1.102-1.126 wherein R₅ is aryl.
1.129. A compound of Formula IV or 1.102-1.126 or 1.128 wherein R₅ is phenyl or tolyl.
1.130. A compound of Formula IV or 1.102-1.126 or 1.128 wherein R₅ is phenyl.
1.131. A compound of Formula IV or 1.102-1.126 or 1.128 wherein R₅ is tolyl.
1.132. A compound of Formula IV or 1.102-1.126 wherein R₅ is lower (e.g. $C_{1-4}$) alkyl
1.133. A compound of Formula IV or 1.102-1.126 or 1.132 wherein R₅ is methyl, ethyl, or propyl.
1.134. A compound of Formula IV or 1.102-1.126 or 1.132 wherein R₅ is methyl.
1.135. A compound of Formula IV or 1.102-1.126 or 1.132 wherein R₅ is ethyl.
1.136. A compound of Formula IV or 1.102-1.126 or 1.132 wherein R₅ is propyl.

Compounds of Formula I, II, III, and IV preferably bind to the nicotinic acetylcholine receptor with a high affinity, e.g., with a $K_D$ binding affinity of less than 10 nM, preferably less than 1 nM.

For example, compounds 1-18 have a $K_D$ binding affinity of 0.7 nM or less.

In one aspect of the present invention the general synthesis of compound of Formula I wherein R₄ is lower alkyl is depicted in exemplary Scheme 1. Eleven mg of compound wherein R₄ is not present and 6 μL methyl iodide (CH₃I) are dissolved in 1.0 mL acetone at room temperature. Under stirring, 8.0 mg K₂CO₃ is added and the mixture is stirred overnight at room temperature. The white solid is filtrated and the solution is concentrated to leave the residue as colorless oil. In the example depicted, the residue is purified on HPLC to give 9.0 mg of the product as colorless oil and with purity>98% and yield about 79%.

The term "alkyl" includes both straight and branched chain alkyl groups. References to individual alkyl groups such as "propyl" are specific to the straight chain version only and references to individual branched chain alkyl groups such as "isopropyl" are specific for the branched version only. For example "$C_{1-6}$ alkyl" includes $C_{1-4}$ alkyl, $C_{1-3}$ alkyl, propyl, isopropyl and t-butyl. A similar convention applies to other radicals, for example "phenyl $C_{1-6}$ alkyl" includes phenyl $C_{1-4}$ alkyl, benzyl, 1-phenylethyl and 2-phenylethyl. "$C_0$alkyl" refers to the hydrogen terminus when the $C_0$alkyl is terminal and refers to a direct bond when the "$C_0$alkyl" is bridging. The term "$C_0$alkyl" for example, refers to adding "$C_0$alkyl" to the scope of the "$C_{1-6}$alkyl" definition. Thus, it is understood that substituents allowed for "$C_{1-6}$alkyl" would accordingly be allowed for the "$C_{1-6}$alkyl" within the scope of the "$C_{0-6}$alkyl".

The term "halo" refers to fluoro, chloro, bromo, and iodo.

Where optional substituents are chosen from, for example, "1-5 independent" substituents from a list of substituents, it is to be understood that this definition includes all substituents being chosen from one of the specified groups or the substituents being chosen from two or more of the specified groups in the list. Where a substituent is recited using the molecule (parent) name, it is understood that the substituent is the radical or such molecular parent.

According to a further aspect of the invention there is provided a pharmaceutical composition which comprises a compound of Formula I, Formula II, Formula III, or Formula IV, e.g. any of 1.1-1.136, in free or pharmaceutically acceptable salt thereof, as defined hereinbefore, in association with a pharmaceutically acceptable diluent or carrier.

The composition may be in a form suitable for oral administration, for example as a tablet or capsule, for parenteral injection (including intravenous, subcutaneous, intramuscular, or infusion) as a sterile solution, suspension or emulsion, for topical administration as an ointment or cream or for rectal administration as a suppository.

In general the above compositions may be prepared in a conventional manner using conventional excipients.

Scheme 1.

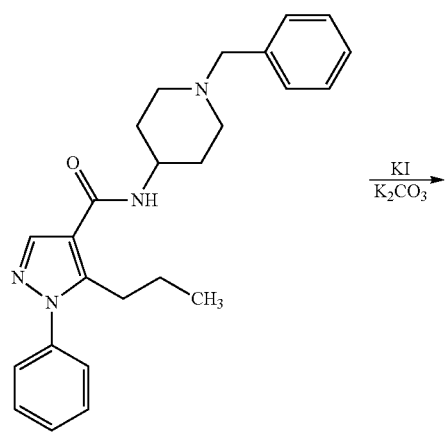

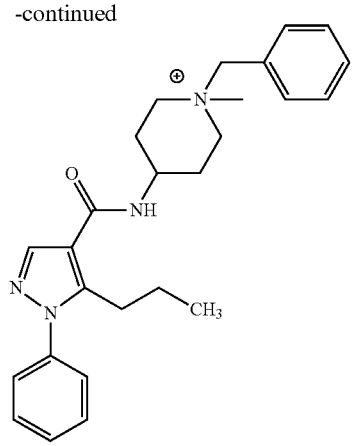

In another aspect of the present invention the general synthesis of a triazole compound of Formula I is depicted in Scheme 2. In this example, Compound 1 of the Scheme 2 is coupled with compound 2 of Scheme 2 at the presence of an activating agent BOP to give product 3 of Scheme 2, which then alkylated with substituted benzyl bromide 4 of Scheme 2 to produce the desired product 6 of Scheme 2 and by product 5 of Scheme 2. Compound 6 of Scheme 2 is purified by a silica gel column and then reacted with TFA to cleave the Boc group. Compound 7 of Scheme 2 is alkylated with benzyl bromide, and the reaction mixture is purified by HPLC to yield final product compound of Formula I, which in the exemplified scheme is a white solid with purity>98%, overall yield about 32%.

Scheme 2.

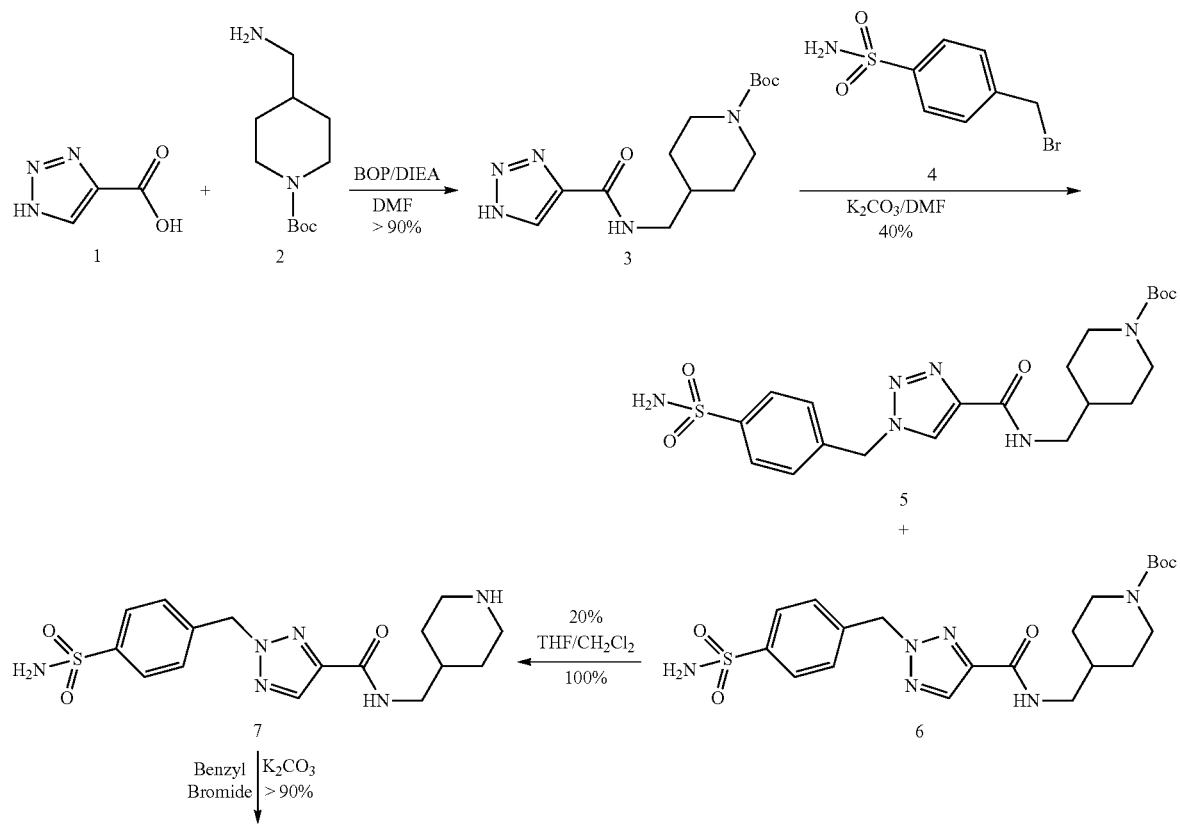

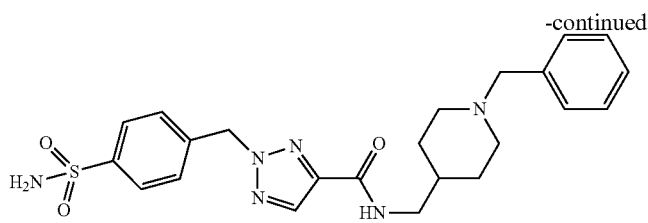
-continued

In another aspect of the present invention the general synthesis of a triazole compound of Formula I is depicted in Scheme 3. In step 1, a coupling reagent, such as BOP, PyBOP, HBTU, HBPyU, DCC and EDC, can be used. In step 2, the N2-substituted triazole intermediate is obtained as the major product. N1-substituted isomer can be removed during purification. After Boc deprotection with TFA (step 3), the obtained intermediate is reacted with $R^4X$ under basic conditions to give the N2-substituted final product. $R^2$ may also be introduced by alkylating Int2 ($R^2$=H) with $R^2X$ in the presence of a base.

ing to Formula I, Formula II, Formula III, or Formula IV (e.g. 1.1-1.137; [0030]-[0034]) in a free or pharmaceutically acceptable salt form, for example:

1.1 Method I, wherein said disease or disorder is small cell lung cancer.
1.2 Method I wherein said disease or disorder is non-small cell lung cancer.
1.3 Method I, wherein said disease or disorder is organophosphorus nerve agent intoxication
1.4 Method I, wherein said disease or disorder is infection via the human immunodeficiency virus (HIV).

Scheme 3

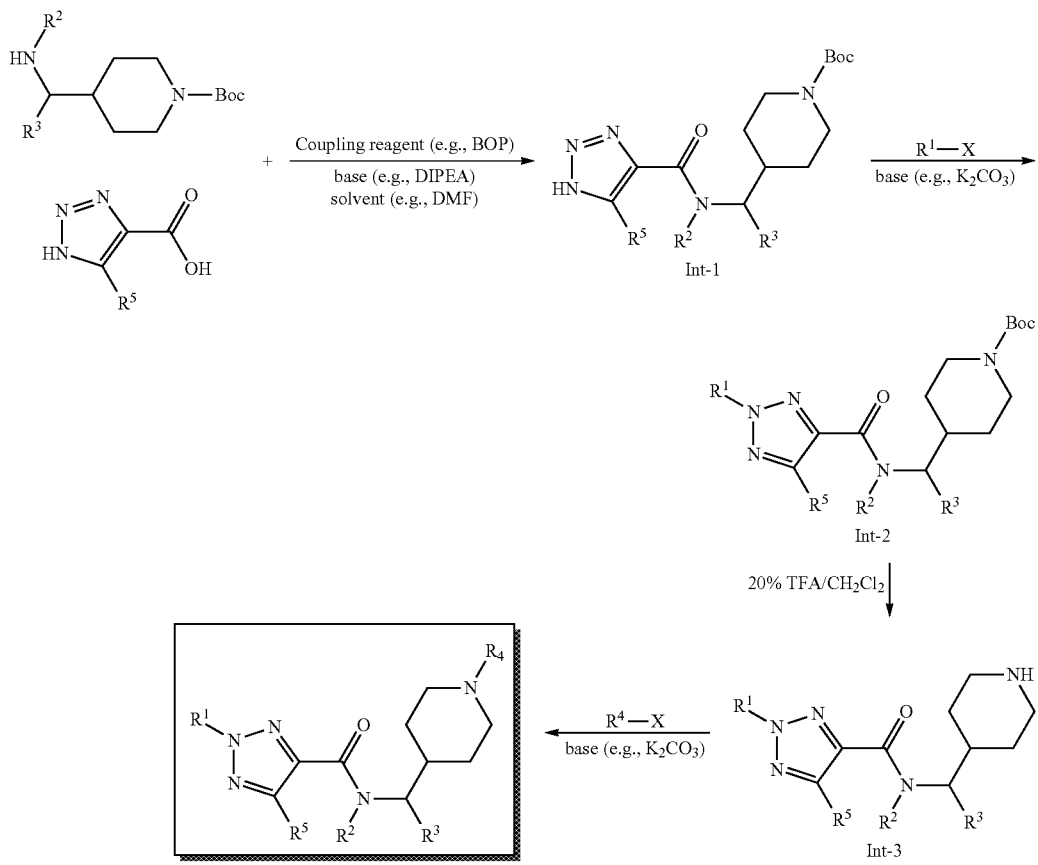

Other Compounds of Formulas I and III are made analogously.

The present invention also provides Method I for the treatment or prophylaxis of a disease or disorder characterized by the activation of an acetylcholine receptor pathway, comprising administering to the patient an effective amount of a α7 nicotinic acetylcholine receptor antagonists accord- 1.5 Method I, wherein said disease or disorder is the result of autoimmune deficiency syndrome (AIDS).
1.6 Method I, or any of methods 1.1-1.5, wherein the patient is a human.
1.7 Method I, or any of methods 1.1-1.6, wherein the disease or disorder is characterized by metastatic cancerous cells.

1.8 Method I, or any of methods 1.1-1.7, wherein the disease or disorder is characterized by benign cancerous cells.

1.9 Method I, or any of methods 1.1-1.8, wherein said disease or disorder characterized by the presence of cancerous cells may be selected from the following group of diseases or disorders: squamous cell carcinoma, adenocarcinoma, large cell carcinoma, and pleuroa mesothelioma.

1.10 Method I, or any of methods 1.1-1.9, wherein said disease or disorder is a solid tumor carcinoma.

1.11 Method I, or any of methods 1.1-1.10, wherein a patient is suffering from or at risk for developing cancer.

1.12 Method I, or any of methods 1.1-1.11, wherein a patient is administered an effective amount of a novel α7 nicotinic acetylcholine receptor antagonist of Formula I, II, III, or IV in a pharmaceutically acceptable carrier.

1.13 Method I, or any of methods 1.1-1.12, wherein a novel α7 nicotinic acetylcholine receptor antagonist of Formula I is administered simultaneously with a second treatment for cancer selected from the group consisting of: capecitabine, trastuzumab, pertuzumab, cisplatin and irinotecan.

1.14 Method I or 1.12, wherein the disease or disorder is a cognitive impairment and/or a disease or disorder related to cognitive impairment.

1.15 Method I or 1.12, 1.14, wherein the cognitive related disease or disorder is mild cognitive impairment 1.16 Method I or 1.12, 1.14-1.15, wherein the α7 nicotinic acetylcholine receptor antagonists according to Formula I or Formula II are used to treat at least one of the symptoms of cognitive impairment, e.g. impaired auditory processing and attention, impaired spatial organization, impaired verbal learning, impaired semantic and verbal memory, impaired executive functions.

1.17 Method I or any of 1.12, 1.13-1.16 wherein the disease or disorder is Alzheimer's disease.

1.18 Method I or any of 1.12, 1.13-1.17, wherein the effective amount of an α7 nicotinic acetylcholine receptor antagonist is used to treat at least one symptom of Alzheimer's disease.

1.19 Method I or 1.12 or 1.18, wherein the symptom of Alzheimer's disease is cognitive impairment, e.g., impaired auditory processing and attention, impaired spatial organization, impaired verbal learning, impaired semantic and verbal memory, impaired executive functions.

1.20 Method I, or any of the preceeding methods wherein the treatment is directed toward smoking cessation in a patient.

1.21 Method I or any of methods 1.12, 1.13-1.16 wherein the α7 nicotinic acetylcholine receptor antagonist is used to treat psychosis, e.g., in schizophrenia, schizoaffective disorder, schizophreniform disorder, psychotic disorder, delusional disorder, mania or bipolar disorder.

1.22 Method I, or any of the preceding methods wherein cognitive impairment is any of the following, e.g., impaired auditory processing and attention, impaired spatial organization, impaired verbal learning, impaired semantic and verbal memory, impaired executive functions.

1.23 Method I, or any of the preceding methods, wherein the cognitive impairment is a symptom of the psychosis, e.g., schizophrenia, schizoaffective disorder, schizophreniform disorder, psychotic disorder, delusional disorder, mania or bipolar disorder.

1.24 Method I or any of the preceding methods wherein the patient is administered an effective amount of an α7 nicotinic acetylcholine receptor antagonist according to Formula I.

1.25 Method I or any of the preceding methods wherein the patient is administered an effective amount of an α7 nicotinic acetylcholine receptor antagonist according to Formula II.

1.26 Method I, or any the preceding methods, wherein a patient is administered an effective amount of a novel α7 nicotinic acetylcholine receptor antagonist of Formula I in a pharmaceutically acceptable carrier.

1.27 Method I or any of the preceding methods wherein the patient is administered an effective amount of an α7 nicotinic acetylcholine receptor antagonist according to Formula I, e.g., selected from compounds 1-18.

1.28 Method I or any of the preceding methods wherein administered an effective amount of any of the compounds of Formula I, II, III, or IV (e.g. 1.1-1.136) improves cognition.

Again, it is contemplated that any of the compounds disclosed herein of Formula I, II, III, or IV (e.g. 1.1-1.136; [0031]-[0036]) may be used with any of the methods disclosed herein (e.g. Method I or 1.1-1.28).

The selectivity of these compounds is measured on the neuronal α4β2 and the muscle-type nAChRs using methods known in the art. At 10 μM, all tested compounds show selectivity for the α7 nAChR over other two nicotinic receptors. Compound 16, for example, exhibits 92% binding to the α7 receptor and no detectable binding to the neuronal α4β2 and muscle-type nAChRs.

The pharmacokinetic (PK) study of compounds are performed in male C57Bl/6 mice (n=3 per time point) after an oral administration at 10 mg/kg to evaluate the brain penetrability. The concentrations of representative Compound 16 in brain and plasma are 0.15 μM and 0.2 μM at time t=2 h, respectively. The $t_{max}$ of Compound Q is probably longer than 2 h.

Three-dimensional structural models of human α7 nAChR are developed using homology modeling based on a known antagonist bound A-AChBP crystal structures. Docking studies are conducted to predict the binding poses of these novel nicotinic antagonists.

In accordance with this detailed description, the following abbreviations and definitions apply. It must be noted that as used herein, the singular forms "a", "and", and "the" include plural referents unless the context clearly dictates otherwise. Thus, for example, reference to "a compound" includes a plurality of such compounds and reference to "the dosage" includes reference to one or more dosages and equivalents thereof known to those skilled in the art, and so forth.

The terms "treating", "treatment", and the like are used herein to generally mean obtaining a desired pharmacological and physiological effect. The novel α7 nAChRs described herein which are used to treat a subject with cancer generally are provided in a therapeutically effective amount to achieve any one or more of the following: inhibited tumor growth, reduction in tumor mass, loss of metastatic lesions, inhibited development of new metastatic lesions after treatment has started, or reduction in tumor such that there is no detectable disease (as assessed by, e.g., radiologic imaging, biological fluid analysis, cytogenetics, fluorescence in situ hybridization, immunocytochemistry, colony assays, multiparameter flow cytometry, or polymerase chain reaction). The term "treatment", as used herein, covers any treatment of a disease in any mammal, particularly a human, known to those that are skilled in the art The term "subject" or "patient" as used herein is meant to include a mammal. In a preferred aspect of the present invention the mammal is a human. In another preferred aspect of the present invention the mammal is a domestic animal.

The term "pharmaceutically effective" as used herein refers to the effectiveness of a particular treatment regime. Pharmaceutical efficacy can be measured based on such characteristics, for example, as: inhibition of tumor growth, reduction of tumor mass or rate of growth, lack of detectable tumor associated antigens, and any other diagnostic measurement tool that is known in the field. Pharmaceutical efficacy can also be measured based on such characteristics, for example, as: inhibition of the HIV virus and/or reduction and eradication of AIDS related symptoms. Moreover, pharmaceutical efficacy can also be measured based upon the reduction of the onset of symptoms that are related to the induction of organophosphorus nerve agent intoxication.

By "pharmaceutically effective amount" as used herein refers to the amount of an agent, reagent, compound, composition, or combination of reagents disclosed herein that when administered to a mammal that are determined to be sufficiently effective against cancer that is the object of the treatment or HIV/AIDS. A pharmaceutically effective amount will be known to those skilled in the art.

By the term "tumor" is meant to include both benign and malignant growths or cancer. The term "cancer," is meant to encompass, unless otherwise stated, both benign and malignant growths. In preferred aspects of the invention the tumor referred to is malignant. The tumor can be a solid tissue tumor such as a melanoma, or a soft tissue tumor such as a lymphoma, a leukemia, or a bone cancer. By the term "primary tumor" is meant the original neoplasm and not a metastatic lesion located in another tissue or organ in the patient's body. By the terms "metastatic disease," "metastases," and "metastatic lesion" are meant a group of cells which have migrated to a site distant relative to the primary tumor.

By "AIDS" is meant HIV infection: AIDS, ARC (AIDS related complex), both symptomatic and asymptomatic, and actual or potential exposure to HIV. Accordingly, the treatment of AIDS refers to the inhibition of HIV virus, the prophylaxis or treatment of infection by HIV and the prophylaxis, treatment or the delay in the onset of consequent pathological conditions such as AIDS. The prophylaxis of AIDS, treating AIDS, delaying the onset of AIDS, the prophylaxis of infection by HIV, or treating infection by HIV is defined as including, but not limited to, treatment of a wide range of states of HIV infection: AIDS, ARC (AIDS related complex), both symptomatic and asymptomatic, and actual or potential exposure to HIV.

The term "nicotinic acetylcholine receptor" refers to the endogenous acetylcholine receptor having binding sites for acetylcholine which also bind to nicotine. The term "nicotinic acetylcholine receptor" includes the term "neuronal nicotinic acetylcholine receptor."

The terms "subtype of nicotinic acetylcholine receptor," and "nicotinic acetylcholine receptor subtype" refer to various subunit combinations of the nicotinic acetylcholine receptor, and may refer to a particular homomeric or heteromeric complex, or multiple homomeric or heteromeric complexes.

The term "agonist" refers to a substance that interacts with a receptor and increases or prolongs a physiological response (i.e. activates the receptor).

The term "partial agonist" refers to a substance that interacts with and activates a receptor to a lesser degree than an agonist.

The term "antagonist" refers to a substance that interacts with and decreases the extent or duration of a physiological response of that receptor.

The terms "disorder," "disease," and "condition" are used inclusively and refer to any status deviating from normal.

The term "central nervous system associated disorders" includes any cognitive, neurological, and mental disorders causing aberrant or pathological neural signal transmission, such as disorders associated with the alteration of normal neurotransmitter release in the brain.

EXAMPLES

The synthetic methods for various compounds of the present invention are illustrated below. Other compounds of the invention and their salts may be made using the methods as similarly described below and/or by methods similar to those generally described in the detailed description and by methods known in the chemical art.

Example 1

N-((1-benzylpiperidin-4-yl)methyl)-2-(4-sulfamoyl-benzyl)-2H-1,2,3-triazole-4-carboxamide

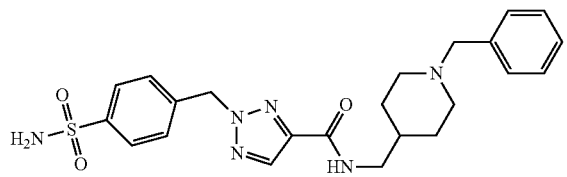 [SMILES: NS(=O)(=O)c1ccc(Cn2ncc(C(=O)NCC3CCN(Cc4ccccc4)CC3)n2)cc1]

(a) tert-butyl 4-((1H-1,2,3-triazole-4-carboxamido)methyl)piperidine-1-carboxylate To a solution of 1H-1,2,3-triazole-4-carboxylic acid (113 mg, 1.0 m mol) and tert-butyl 4-(aminomethyl)piperidine-1-carboxylate (256 mg, 1.2 mmol) in DMF (1.5 mL) is added BOP (530 mg, 1.2 mmol), followed by DIPEA (0.48 mL). The reaction mixture is stirred at room temperature overnight. The solvent is removed under reduced pressure, and the residue is treated with saturated sodium bicarbonate aqueous solution, followed by extraction with methylene and methanol (10:1, v/v). The combined organic phase is evaporated to dryness to give crude product, which is used in the next step without further purification. MS (ESI) m/z 210.1 [M-Boc+H]$^+$ (b) tert-butyl 4-((2-(4-sulfamoylbenzyl)-2H-1,2,3-triazole-4-carboxamido)methyl)piperidine-1-carboxylate A suspension of crude tert-butyl 4-((1H-1,2,3-triazole-4-carboxamido)methyl)piperidine-1-carboxylate (350 mg), 4-(bromomethyl)benzenesulfonamide (340 mg, 1.4 mmol) and potassium carbonate (312 mg, 2.3 mmol) in DMF (8 mL) is stirred at room temperature overnight. After routine workup, the obtained crude product is purified on a silica gel column to give 222 mg of product as a white solid. MS (ESI) m/z 379.1 [M-Boc+H]+

(c) N-(piperidin-4-ylmethyl)-2-(4-sulfamoylbenzyl)-2H-1,2,3-triazole-4-carboxamide tert-butyl 4-((2-(4-sulfamoylbenzyl)-2H-1,2,3-triazole-4-carboxamido)methyl)piperidine-1-carboxylate (116 mg, 0.24 mmol) in 10% TFA/CH$_3$CN (3 mL) is stirred at room temperature for 2 h. The solvent is removed under reduced pressure, and the residue is further dried with a high vacuum pump to give 170 mg of crude product as a TFA salt, which is used in the next step without further purification. MS (ESI) m/z 379.1 [M+H]+

(d) N-((1-benzylpiperidin-4-yl)methyl)-2-(4-sulfamoylbenzyl)-2H-1,2,3-triazole-4-carboxamide A suspension of crude N-(piperidin-4-ylmethyl)-2-(4-sulfamoylbenzyl)-2H-1,2,3-triazole-4-carboxamide (45 mg), benzyl bromide (22 µL) and potassium carbonate (82 mg) in DMF (2 mL) is stirred at room temperature for 2 h. The reaction mixture is filtered through a microfilter, and the filtrate was purified with a preparative HPLC to give 17 mg of pure product as a white solid. MS (ESI) m/z 469.2 [M+H]+

Example 2

N-((1-(4-fluorobenzyl)piperidin-4-yl)methyl)-2-(4-sulfamoylbenzyl)-2H-1,2,3-triazole-4-carboxamide

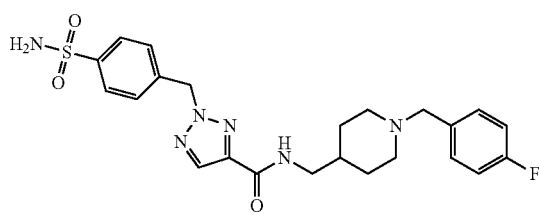 [SMILES: NS(=O)(=O)c1ccc(Cn2ncc(C(=O)NCC3CCN(Cc4ccc(F)cc4)CC3)n2)cc1]

This compound is prepared using the procedure analogous to example 1 wherein 4-fluorobenzyl bromide is added in step (d) instead of benzyl bromide. Product is obtained as a white solid with 98% purity (yield: 81%). MS (ESI) m/z 487.2 [M+H]+.

Example 3

N-((1-(2,4-dichlorobenzyl)piperidin-4-yl)methyl-2-(4-sulfamoylbenzyl)-2H-1,2,3-triazole-4-carboxamide

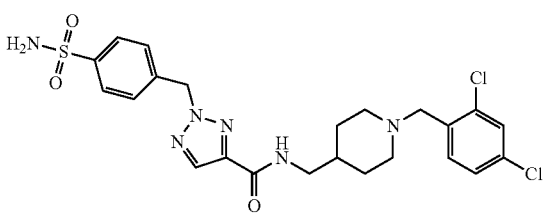 [SMILES: NS(=O)(=O)c1ccc(Cn2ncc(C(=O)NCC3CCN(Cc4ccc(Cl)cc4Cl)CC3)n2)cc1]

This compound is prepared using the procedure analogous to example 1 wherein 2,4-dichlorobenzyl bromide is added in step (d) instead of benzyl bromide. Product is obtained as a white solid with 95% purity (yield: 62%). MS (ESI) m/z 537.2 [M+H]+.

Example 4

N-((1-(2-chlorobenzyl)piperidin-4-yl)methyl)-2-(4-sulfamoylbenzyl)-2H-1,2,3-triazole-4-carboxamide

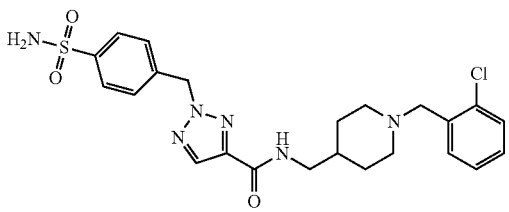 [SMILES: NS(=O)(=O)c1ccc(Cn2ncc(C(=O)NCC3CCN(Cc4ccccc4Cl)CC3)n2)cc1]

This compound is prepared using the procedure analogous to example 1 wherein 2-chlorobenzyl bromide is added in step (d) instead of benzyl bromide. Product is obtained as a white solid with 98% purity (yield: 55%). MS (ESI) m/z 503.2 [M+H]+.

Example 5

N-((1-(4-methylbenzyl)piperidin-4-yl)methyl)-2-(4-sulfamoylbenzyl)-2H-1,2,3-triazole-4-carboxamide

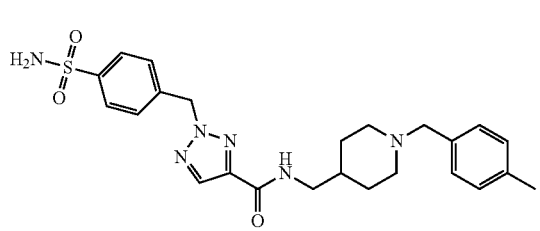 [SMILES: Cc1ccc(CN2CCC(CNC(=O)c3cnn(Cc4ccc(S(N)(=O)=O)cc4)n3)CC2)cc1]

This compound is prepared using the procedure analogous to example 1 wherein 4-methylbenzyl bromide is added in step (d) instead of benzyl bromide. Product is obtained as a white solid with 96% purity (yield: 73%). MS (ESI) m/z 483.2 [M+H]+.

Example 6

N-((1-(4-chlorobenzyl)piperidin-4-yl)methyl)-2-(4-sulfamoylbenzyl)-2H-1,2,3-triazole-4-carboxamide

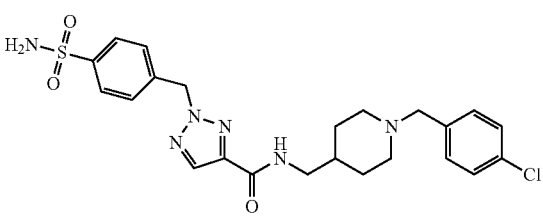 [SMILES: NS(=O)(=O)c1ccc(Cn2ncc(C(=O)NCC3CCN(Cc4ccc(Cl)cc4)CC3)n2)cc1]

This compound is prepared using the procedure analogous to example 1 wherein 4-chlorobenzyl bromide is added in step (d) instead of benzyl bromide. Product is obtained as a white solid with 97% purity (yield: 84%). MS (ESI) m/z 503.2 [M+H]⁺.

Example 7

N-((1-(3-chlorobenzyl)piperidin-4-yl)methyl)-2-(4-sulfamoylbenzyl)-2H-1,2,3-triazole-4-carboxamide

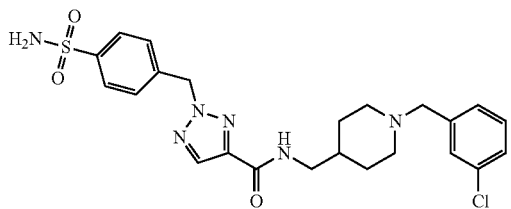 [SMILES: NS(=O)(=O)c1ccc(Cn2ncc(C(=O)NCC3CCN(Cc4cccc(Cl)c4)CC3)n2)cc1]

This compound is prepared using the procedure analogous to example 1 wherein 3-chlorobenzyl bromide is added in step (d) instead of benzyl bromide. Product is obtained as a white solid with 95% purity (yield: 70%). MS (ESI) m/z 503.2 [M+H]⁺.

Example 8

N-((1-(3-chlorobenzyl)piperidin-4-yl)methyl)-2-(4-sulfamoylbenzyl)-2H-1,2,3-triazole-4-carboxamide

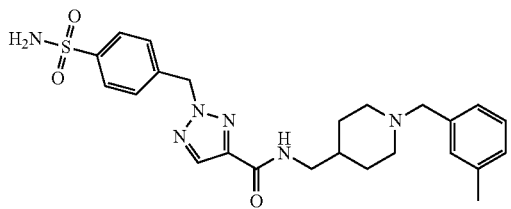 [SMILES: Cc1cccc(CN2CCC(CNC(=O)c3cnn(Cc4ccc(S(N)(=O)=O)cc4)n3)CC2)c1]

This compound is prepared using the procedure analogous to example 1 wherein 3-methylbenzyl bromide is added in step (d) instead of benzyl bromide. Product is obtained as a white solid with 97% purity (yield: 83%). MS (ESI) m/z 483.2 [M+H]⁺.

Example 9

4-((4-((1-benzylpiperidin-4-yl)methylcarbamoyl)-2H-1,2,3-triazol-2-yl)methyl)benzoic acid

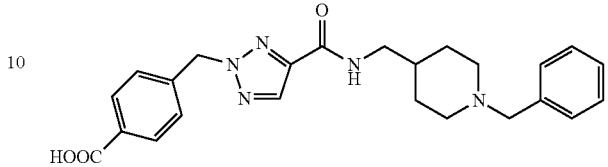

This compound is prepared using the procedure analogous to example 1 wherein 4-(bromomethyl)benzoic acid is added in step (b) instead of 4-(bromomethyl)benzenesulfonamide. Product is obtained as a white solid with 98% purity. MS (ESI) m/z 434.2 [M+H]⁺.

Example 10

α7 Receptor Binding

Receptor binding assays are performed using previously established methods known the art. Briefly, the binding affinity for the α7 receptor is measured on rat brain membranes with [$^{125}$I]α-Bungarotoxin (α-BTX) as the radioligand. Representative data may be seen in Table 1. The binding affinity for the α4β2 receptor is performed on rat cortical membranes using [$^{3}$H]epibatidine as the radioligand. The muscle-type nAChR binding is determined using human TE671 cells with [$^{125}$I]α-BTX as the radioligand. The compounds are first screened at single concentration (10 µM) and then at multiple concentrations to determine IC$_{50}$s if they exhibited promising receptor binding in the primary screening.

α7 nAChR binding is discussed in

TABLE 1

α7 nAChR Inhibition of Diazole Compounds of Formula I.

| R₁ | R₂ | R₃ | R₄ | % Inhibition at 10 µM |
|---|---|---|---|---|
| H | H | Propyl | — | **** |
| 4-SO₂NH₂ | 4-Cl | Propyl | — | * |
| 4-SO₂NH₂ | H | Phenyl | — | * |
| 4-COOH | H | Phenyl | — | * |
| H | 4-COOH | Propyl | — | *** |
| H | H | Propyl | Methyl | *** |

\* = 1-25%  
\*\* = 25-50%  
\*\*\* = 50-75%  
\*\*\*\* = 75-100%

TABLE 2

α7 nAChR Inhibition of triazole compounds of Formula I

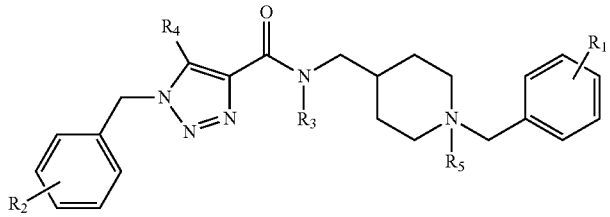

Core A

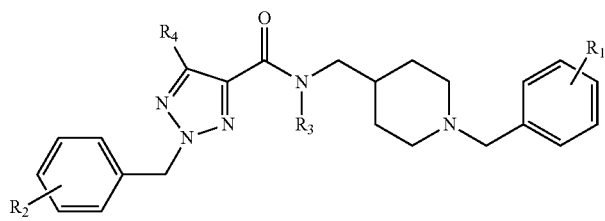

Core B

| Core | $R_1$ | $R_2$ | $R_3$ | $R_4$ | $R_5$ | % Inhibition at 10 μM |
|---|---|---|---|---|---|---|
| A | H | 2-Cl | Methyl | H | — | **** |
| A | H | 3-Cl | H | H | — | **** |
| A | 4-SO$_2$NH$_2$ | H | H | H | — | * |
| A | H | 2-Cl,4- | Methyl | H | — | ** |
| A | H | 4-SO$_2$NH$_2$ | H | H | — | *** |
| A | 4-SO$_2$NH$_2$ | H | H | Ethyl | — | * |
| A | 4-SO$_2$NH$_2$ | 2-Methyl | H | Ethyl | — | * |
| A | 4-COOH | H | H | Ethyl | — | * |
| A | 4-COOH | 2-Methyl | H | Ethyl | — | * |
| A | H | 4-COOH | H | H | — | * |
| B | H | 4-SO$_2$NH$_2$ | H | H | — | **** |
| B | H | 4-COOH | H | H | — | *** |
| A | H | 2-Cl | Methyl | H | Methyl | ** |

\* = 1-25%
\*\* = 25-50%
\*\*\* = 50-75%
\*\*\*\* = 75-100%

The selectivity of these compounds is measured on the neuronal α4β2 and the muscle-type nAChRs using previously disclosed and known in the art. At 10 μM, all tested compounds showed selectivity for the α7 nAChR over other two nicotinic receptors.

Example 11

α7 Receptor Functional Assay

The receptor functional assays use previously established fluorescent assays known in the art. Briefly, human neuroblastoma cell line expressing endogenous nicotinic receptors may be used in this study. Ca$^{2+}$-sensitive dye is used to monitor the Ca$^{2+}$ signal changes caused by tested compounds. Epibatidine and mecamylamine are used as the positive controls for the agonist and antagonist determination assays, respectively.

The functional activity of representative compounds is determined by measuring calcium (Ca$^{2+}$) fluorescence signals on human neuroblastoma cell line cells expressing endogenous nicotinic receptors. Agonist-induced activation of nicotinic receptors may lead to the increase in intracellular Ca$^{2+}$ levels, while nicotinic antagonists could result in the decrease in intracellular Ca$^{2+}$ concentrations. Ca$^{2+}$ sensitive dye fluo-3 is widely used to monitor the intracellular Ca$^{2+}$ concentration changes caused by nicotinic ligands and to identify the agonism vs antagonism. Compounds disclosed can inhibit epibatidine-evoked Ca$^{2+}$ fluorescence response in a dose-dependent manner. This suggests the subject compounds are nAChR antagonists.

Example 12

Pharmacokinetics

Male, 8-10 week-old C57/BLC mice are used in this experiment. All handling and use follows a protocol of Institutional Animal Care and Use Committee of Columbia University, in accordance with NIH guidelines. The vehicle comprises 5% DMSO, 5% Tween-20, 15% PEG400 and 75% dH2O. Compounds are co-injected to the animals (N≥3) at 10 mg/kg dose via an oral (p.o.) administration. After various time periods (0.25, 0.5, 1, 2, 4 h), animals are sacrificed and blood and brain collected. Whole brains are collected and frozen in pre-weighed Eppendorf tubes at −80° C. The brain homogenates are sonicated with PBS buffer (137 mM NaCl, 2.7 mM KCl, 10 mM Phosphate buffer) at pH 7.4, using 2 mL/g (v/w) homogenate. Blood samples are collected from the retro-orbital veins using VWR pasteur pipettes. Blood samples are centrifuged at 60,000 rpm for 40 minutes at 4° C., and the plasma fractions are separated and stored at −80° C. Brain homogenates and plasma are extracted by vertex with 2 volumes of acetonitrile and clarified by centrifugation at 12,000 g for 20 min and then analyzed by HPLC/MS/MS. The HPLC/MS/MS system included a Waters Alliance 2675 separations module and a Micromass Quattro-Micro Mass Spectrometer. Separation is achieved on the column (2.1×50 mm) of Synergi 4μ Fusion-RP with a gradient of 10 mM ammonium acetate in methanol from 40%~100% within 3 min. Sample injection volume is 10 μl and flow rate was 0.6 ml/min. Control experiments are performed to determine extraction efficiencies.

Example 13

Novel Object Recognition/Object Recognition Test

Animals are housed in individual standard cages on sawdust bedding in an air-conditioned room (about 20° C.). They are kept under a 12/12 h light/dark cycle (lights on from 19.00 to 07.00) and have free access to food and water. Rats are housed and tested in the same room. A radio, which plays softly, provides background noise in the room. All testing is done between 09.00 and 17.00 hours.

Compounds disclosed herein are tested at 0, 0.3, 1, and 3 mg/kg in a time-dependent memory deficit model, i.e. a 24 h inter-trial interval. Compounds may be administered by intraperitoneal injection (i.p. injection), 15 minutes-2 h before the first trial. The order of the treatments is balanced to prevent the data from being distorted by potential object- and side-preferences of the animals.

The object recognition test is performed as described elsewhere (e.g., Ennaceur and Delacour, 1988). The apparatus consists of a circular arena, about 83 cm in diameter. The back-half of the about 40 cm high arena wall is made of gray polyvinyl chloride, the front-half consists of transparent polyvinyl chloride. The light intensity is equal in the different parts of the apparatus, as fluorescent red tubes provide a constant illumination of about 20 lux on the floor of the apparatus. Two objects are placed in a symmetrical position at about 10 cm from the wall, on a diameter from the left- to the right-side of the arena. Each object is available in triplicate. Four different sets of objects are used. The different objects are: 1) a cone that consists of a gray polyvinyl chloride base (maximal diameter 18 cm) with a collar on top made of aluminum (total height about 16 cm), 2) a standard 1 L transparent glass bottle (diameter about 10 cm, height about 22 cm) filled with water, 3) a massive metal cube (about 10.0×5.0×7.5 cm) with two holes (diameter about 1.9 cm), and 4) a solid aluminum cube with a tapering top (13.0×8.0×8.0 cm). Rats are unable to displace the objects.

A testing session consists of two trials. The duration of each trial is 3 min. During the first trial (T1) the apparatus contains two identical objects (samples). Rats are placed in the apparatus facing the wall at the middle of the front (transparent) segment. After the first exploration period the rat is put back in its home cage. Subsequently, after a 24 h delay interval, the rat is put in the apparatus for the second trial (T2). The total time an animal spends exploring each object during T1 and T2 is recorded manually with a personal computer.

Exploration is defined as follows: directing the nose to the object at a distance of no more than 2 cm and/or touching the object with the nose. Sitting on the object is not considered as exploratory behavior. A minimal amount of object interaction is required in order to achieve reliable object discrimination, therefore rats that explore less than 7 s in T1 and/or 9 s in T2 are excluded from the analyses. In order to avoid the presence of olfactory cues the objects are always thoroughly cleaned after each trial. All object combinations as well as the location (left or right) of the novel object are used in a balanced manner to avoid potential biases due to preferences for particular locations or objects.

In the first two weeks, the animals are handled daily and are allowed to become accustomed to the test setup in two days, i.e. they are allowed to explore the apparatus (without any objects) twice for 3 min each day. The rats are adapted to the testing routine after they demonstrate a stable discrimination performance, i.e. good discrimination at 1 h interval and no discrimination at twice for 3 min each day. The rats are adapted to the testing routine until they showed a stable discrimination performance, i.e. a good discrimination at 1 h interval and no discrimination at twice for 3 min each day.

The basic measures are the times spent by rats in exploring an object during T1 and T2. The time spent in exploring the two identical samples will be represented by 'a1' and 'a2'. The time spent in T2 in exploring the sample and new object are represented by 'a' and 'b', respectively. The following variables are calculated: e1=a1+a2, e2=a+b, and d2=(b−a)/e2. E1 and e2 are measures of the total exploration time of both objects during T1 and T2 respectively. d2 is a relative measure of discrimination corrected for exploration activity in the test-trial (e2). Thus, even if a treatment affects exploratory behavior the d2 index will be comparable between conditions.

Treatment of compounds disclosed herein significantly enhances cognition in treated animals, in a dose dependent manner up to about 1.0 mg/kg, in animals with a compound administration 15 minutes prior to T1. Larger doses of compound may decrease cognition in treatment administration 1-hour post T1.

The invention claimed is:

1. A compound of Formula I:

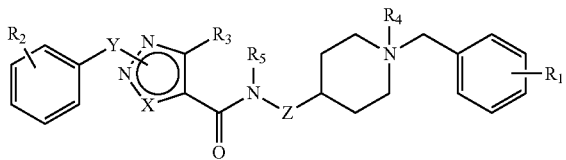

wherein $R_1$ is halogen, —SO$_2$NH$_2$, or —COOH;

$R_2$ is halogen, —SO$_2$NH$_2$, or —COOH, or H;

Y and Z are independently a bond or —CH$_2$—;

X is N or CR$_6$;

R3 and R6 are independently H, phenyl, tolyl, ethyl or propyl;

$R_5$ is independently H, phenyl, tolyl, or lower alkyl;

$R_4$ is lower alkyl, or $R_4$ is not present;

in free or pharmaceutically acceptable salt form;

provided that when $R_4$ is lower alkyl, the compound forms a quaternary ammonium salt and there is an associated pharmaceutically acceptable anion present.

2. A compound selected from the following:
Compound 2
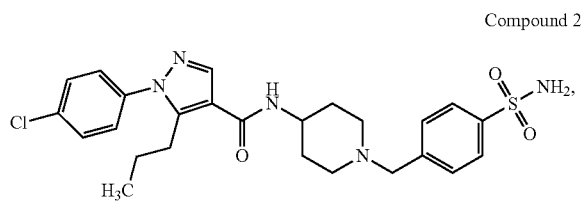
Compound 9
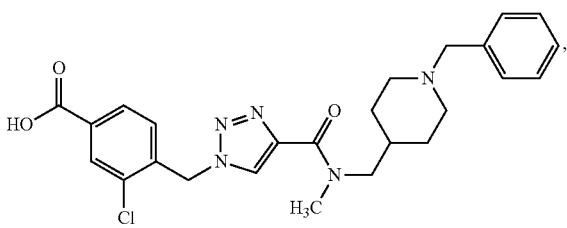
Compound 3
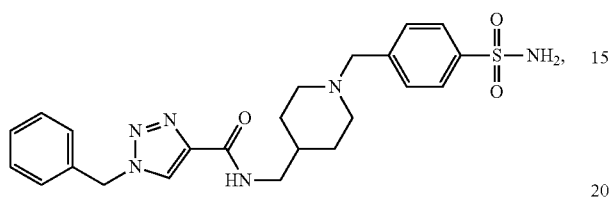
Compound 10
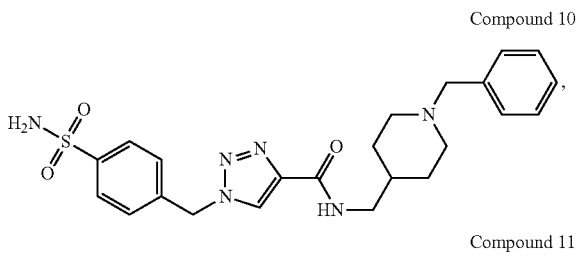
Compound 4
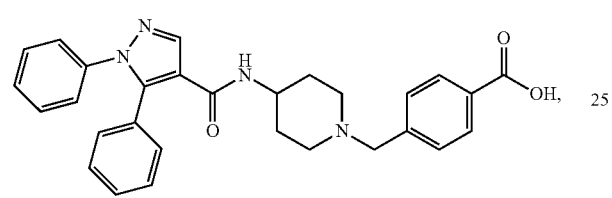
Compound 11
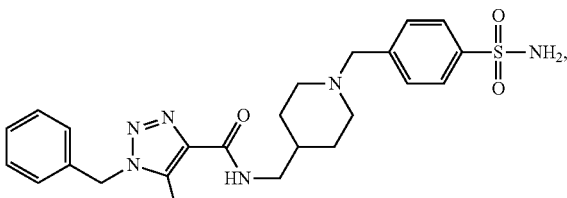
Compound 5
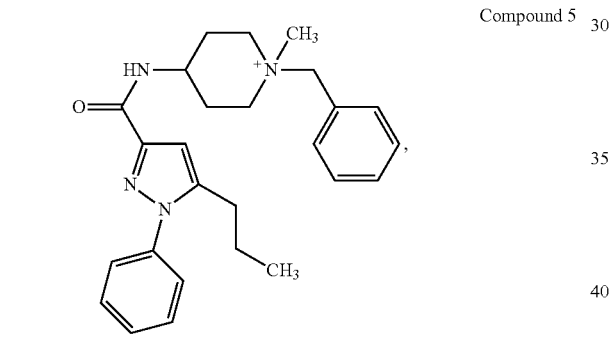
Compound 12
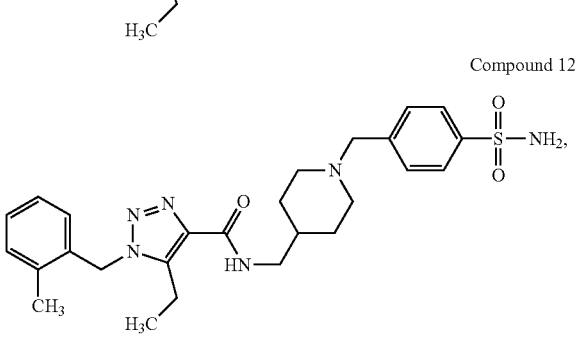
Compound 6
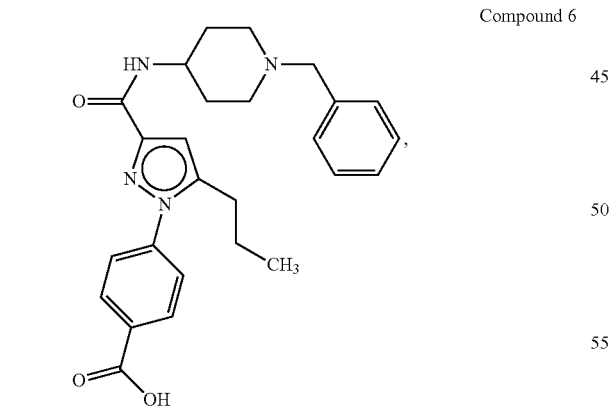
Compound 13
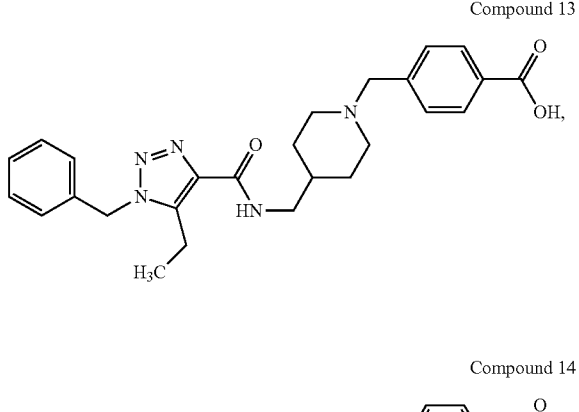
Compound 8
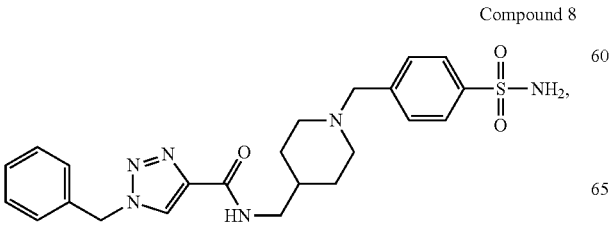
Compound 14
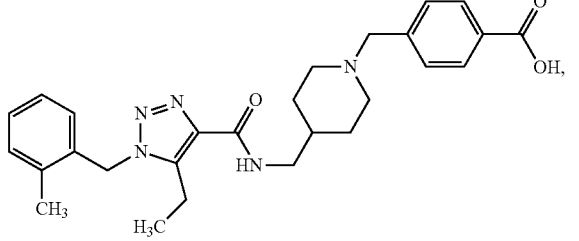

-continued

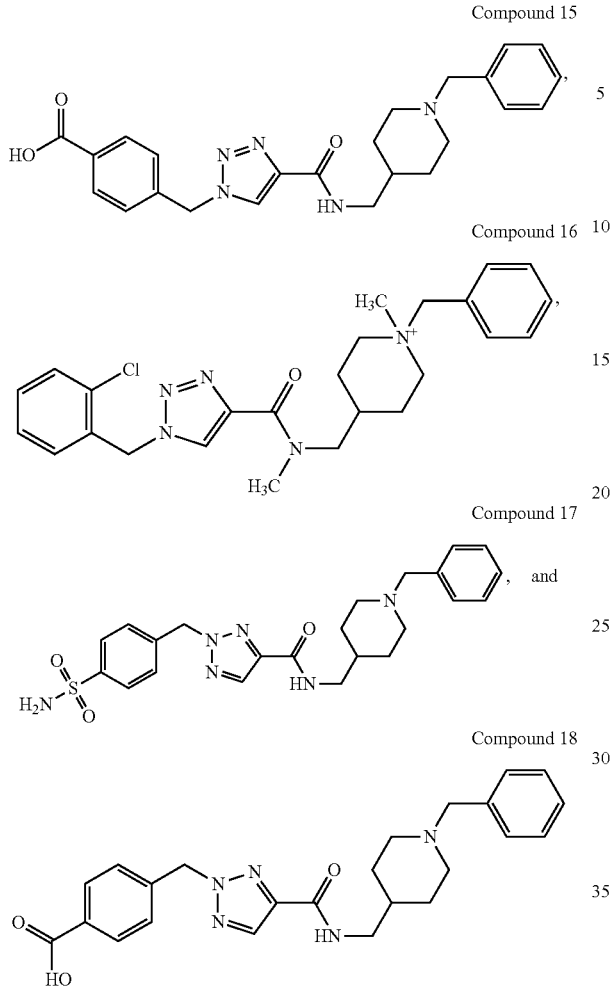

Compound 15

Compound 16

Compound 17

Compound 18 in free or pharmaceutically acceptable salt form.

3. Compound of claim 1, wherein the compound is a compound of Formula

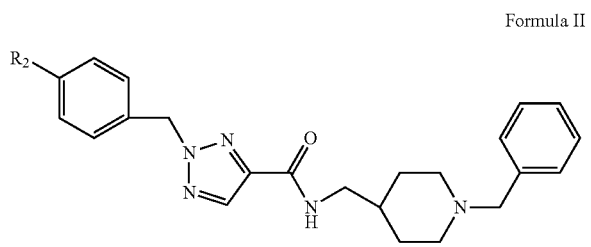

Formula II wherein $R_2$ is halogen, —SO$_2$NH$_2$, or —COOH, in free or pharmaceutically acceptable salt form.

4. A compound of Formula III,

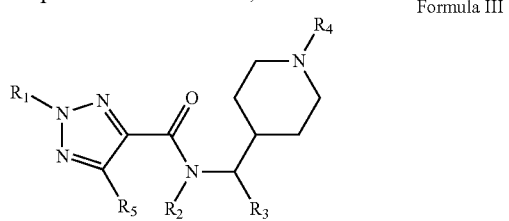

Formula III

Wherein $R_1$ and $R_4$ are independently optionally substituted alkyl, arylalkyl, heteroalkyl, cycloalkyl, cycloalkylalkyl, heteroaryl;

Wherein $R_2$, R3, and $R_5$ are independently H, lower alkyl, aryl;

In free or pharmaceutically acceptable salt form.

5. A compound of claim 3, where the compound is a compound of Formula IV:

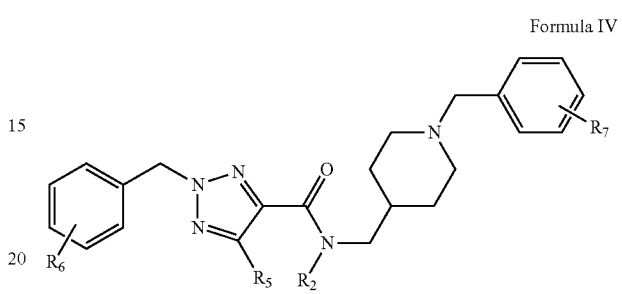

Formula IV

Wherein $R_6$ and $R_7$ are independently halogen, —SO$_2$NH$_2$, or —COOH, or H;

Wherein $R_2$, and $R_5$ are independently H, lower, alkyl, aryl;

In free or pharmaceutically acceptable salt form.

6. A compound according to claim 1 which binds to the nicotinic acetylcholine receptor with an affinity less than 1 nM.

7. A pharmaceutical composition comprising a compound according to claim 1 in admixture with a pharmaceutically acceptable diluent or carrier.

8. A compound according to claim 4 which binds to the nicotinic acetylcholine receptor with an affinity less than 1 nM.

9. A pharmaceutical composition comprising a compound according to claim 4 in admixture with a pharmaceutically acceptable diluent or carrier.

10. A method of treatment of a disease or disorder characterized by the activation of an acetylcholine receptor pathway, comprising administering to the patient an effective amount of compound according to claim 1 in a free or pharmaceutically acceptable salt form, wherein said disease or disorder is selected from the group consisting of small-cell lung cancer, non-small cell lung cancer, organophosphorus nerve agent intoxication, human immunodeficiency virus (HIV) infection, acquired immune deficiency syndrome (AIDS), squamous cell carcinoma, adenocarcinoma, large cell carcinoma, pleura mesothelioma, solid tumor carcinoma, cognitive impairment, Alzheimer's disease, psychosis, or a combination thereof, or wherein treatment is directed towards improving cognition, or smoking cessation.

11. A method of claim 10, wherein said disease or disorder is small cell lung cancer or non-small cell lung cancer.

12. A method of claim 10, wherein said disease or disorder is organophosphorus nerve agent intoxication.

13. A method of claim 10, wherein said disease or disorder is selected from squamous cell carcinoma, adenocarcinoma, large cell carcinoma, or pleura mesothelioma.

14. A method of claim 10, wherein said disease or disorder is cognitive impairment, and said cognitive impairment is a symptom of psychosis.

15. A method of claim 10, wherein said disease or disorder is cognitive impairment, and said cognitive impairment is a symptom of Alzheimer's disease.

16. A method of claim 10, wherein said disease or disorder is psychosis, and wherein said psychosis is selected from the group consisting of schizophrenia, schizoaffective disorder, schizophreniform disorder, psychotic disorder, delusional disorder, mania or bipolar disorder.

17. A method of claim 10, wherein the treatment is directed toward improving cognition.

18. A method of treatment of a disease or disorder characterized by the activation of an acetylcholine receptor pathway, comprising administering to the patient an effective amount of compound according to claim 4 in a free or pharmaceutically acceptable salt form, wherein said disease or disorder is selected from the group consisting of small-cell lung cancer, non-small cell lung cancer, organophosphorus nerve agent intoxication, human immunodeficiency virus (HIV) infection, acquired immune deficiency syndrome (AIDS), squamous cell carcinoma, adenocarcinoma, large cell carcinoma, pleura mesothelioma, solid tumor carcinoma, cognitive impairment, Alzheimer's disease, psychosis, or a combination thereof, or wherein treatment is directed towards improving cognition, or smoking cessation.

19. A method of claim 18, wherein said disease or disorder is small cell lung cancer or non-small cell lung cancer.

20. A method of claim 18, wherein said disease or disorder is organophosphorus nerve agent intoxication.

21. A method of claim 18, wherein said disease or disorder is selected from squamous cell carcinoma, adenocarcinoma, large cell carcinoma, or pleura mesothelioma.

22. A method of claim 18, wherein said disease or disorder is cognitive impairment, and said cognitive impairment is a symptom of psychosis.

23. A method of claim 18, wherein said disease or disorder is cognitive impairment, and said cognitive impairment is a symptom of Alzheimer's disease.

24. A method of claim 18, wherein said disease or disorder is psychosis, and wherein said psychosis is selected from the group consisting of schizophrenia, schizoaffective disorder, schizophreniform disorder, psychotic disorder, delusional disorder, mania or bipolar disorder.

25. A method of claim 19, wherein the treatment is directed toward improving cognition.

26. A method of claim 11, wherein said disease is small cell lung cancer.

27. A method of claim 19, wherein said disease is small cell lung cancer.

28. A compound of Formula I:

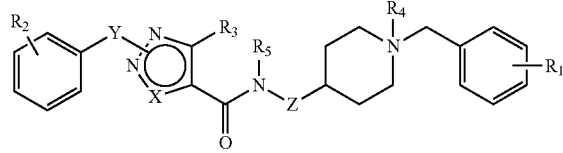

wherein $R_1$ is halogen, —$SO_2NH_2$, or —COOH, or H;
$R_2$ is —$SO_2NH_2$, or —COOH;
Y and Z are independently a bond or —$CH_2$—;
X is N or $CR_6$;
R3 and R6 are independently H, phenyl, tolyl, ethyl or propyl;
$R_5$ is independently H, phenyl, tolyl, or lower alkyl;
$R_4$ is lower alkyl, or $R_4$ is not present;
in free or pharmaceutically acceptable salt form;
provided that when $R_4$ is lower alkyl, the compound forms a quaternary ammonium salt and there is an associated pharmaceutically acceptable anion present.

29. A compound according to claim 28 which binds to the nicotinic acetylcholine receptor with an affinity less than 1 nM.

30. A pharmaceutical composition comprising a compound according to claim 28 in admixture with a pharmaceutically acceptable diluent or carrier.

31. A method of treatment of a disease or disorder characterized by the activation of an acetylcholine receptor pathway, comprising administering to the patient an effective amount of compound according to claim 28 in a free or pharmaceutically acceptable salt form, wherein said disease or disorder is selected from the group consisting of small-cell lung cancer, non-small cell lung cancer, organophosphorus nerve agent intoxication, human immunodeficiency virus (HIV) infection, acquired immune deficiency syndrome (AIDS), squamous cell carcinoma, adenocarcinoma, large cell carcinoma, pleura mesothelioma, solid tumor carcinoma, cognitive impairment, Alzheimer's disease, psychosis, or a combination thereof, or wherein treatment is directed towards improving cognition, or smoking cessation.

32. A method of claim 31, wherein said disease or disorder is small cell lung cancer or non-small cell lung cancer.

33. A compound of claim 5, wherein $R_2$ and $R_5$ are H, in free or pharmaceutically acceptable salt form.

34. The compound of claim 2, selected from:

Compound 17

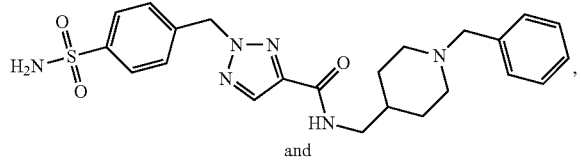

and

Compound 18

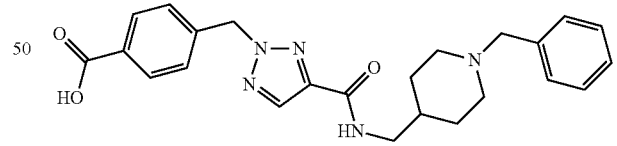

in free or pharmaceutically acceptable salt form.

* * * * *